United States Patent
Goedemoed et al.

[19]

[11] Patent Number: 5,980,948
[45] Date of Patent: Nov. 9, 1999

[54] POLYETHERESTER COPOLYMERS AS DRUG DELIVERY MATRICES

[75] Inventors: Jaap H. Goedemoed, Amsterdam; Wim E. Hennink, Waddinxveen, both of Netherlands

[73] Assignee: Osteotech, Inc., Eatontown, N.J.

[21] Appl. No.: 08/699,896

[22] Filed: Aug. 16, 1996

[51] Int. Cl.⁶ .............................. A61K 47/34; A61K 9/14
[52] U.S. Cl. .......................................................... 424/489
[58] Field of Search ..................................... 424/490, 489

[56] References Cited

U.S. PATENT DOCUMENTS

| | | | |
|---|---|---|---|
| 4,237,885 | 12/1980 | Wong et al. ............................. | 128/260 |
| 5,066,772 | 11/1991 | Tang et al. ............................... | 528/354 |
| 5,439,688 | 8/1995 | Orsolini et al. ......................... | 424/489 |
| 5,443,961 | 8/1995 | Atkinson et al. ....................... | 604/892.1 |
| 5,480,436 | 1/1996 | Bakker et al. ........................... | 623/11 |
| 5,567,435 | 10/1996 | Hubbell et al. ......................... | 424/489 |
| 5,585,460 | 12/1996 | Yamada et al. ......................... | 528/491 |
| 5,656,297 | 8/1997 | Bernstein et al. ...................... | 424/484 |
| 5,662,926 | 9/1997 | Wick et al. .............................. | 424/448 |
| 5,676,969 | 10/1997 | Wick et al. .............................. | 424/448 |
| 5,759,563 | 6/1998 | Yewey et al. ........................... | 424/426 |

FOREIGN PATENT DOCUMENTS

| | | |
|---|---|---|
| 266119 | 5/1988 | European Pat. Off. . |
| 333523 | 9/1989 | European Pat. Off. . |
| 603992 | 6/1994 | European Pat. Off. . |
| WO 93/21858 | 11/1993 | WIPO . |
| WO95/02416 | 1/1995 | WIPO . |

*Primary Examiner*—Peter F. Kulkosky
*Attorney, Agent, or Firm*—Banner & Witcoff, Ltd.

[57] ABSTRACT

A composition for delivering a biologically active agent to a host. The composition comprises a product including a biologically active agent encapsulated in a matrix comprising a polyetherester copolymer, such as a polyethylene glycol terephthalate/polybutylene terephthalate copolymer. The polyetherester copolymer protects the biologically active agent (including proteins, peptides, and small drug molecules) from degradation or denaturation, and therefore such copolymers may be employed in a variety of drug delivery systems and vaccines.

48 Claims, 15 Drawing Sheets

(●) volume weight average diameter; (■) number weight average diameter (●) number weight average diameter; (■) volume weight average diameter

POLYETHERESTER COPOLYMERS AS DRUG DELIVERY MATRICES

This invention relates to drug delivery matrices which contain and release a therapeutic agent. More particularly, this invention relates to a pharmaceutical composition which includes a biologically active agent encapsulated in a matrix comprising a polyetherester copolymer, such as, for example, a polyethylene glycol terephthalate/polybutylene terephthalate copolymer.

Considerable research has been undertaken in the field of delivery matrices which contain and deliver various biologically active agents. One reason is to develop delivery systems which prolong the release time of existing drugs. Another reason is that many new drugs which have been developed have poor pharmacokinetic profiles. In particular, peptides and proteins cause pharmacokinetic difficulties. Such substances must be administered parenterally if a systemic action is required. Also, many new drugs have short half lives, which necessitates frequent injection schedules. Patient compliance and the high cost associated with frequent dosing protocols for parenterally administered drugs provide strong stimuli for alternative dosage forms and dosing regimens.

Polymeric systems which presently are under investigation as drug delivery matrices include polylactic acid (PLA) and copolymers of polylactic acid with glycolic acid. Such copolymers also are known as PLGA polymers. (Brannon-Peppas, *Int. J. Pharmaceutics*, Vol. 116, pgs. 1–9 (1995); Couvreur, et al., *Advanced Drug Delivery Reviews*, Vol. 10, pgs. 141–162 (1993).) Conti, et al., *J. Microencapsulation*, Vol. 9, pgs. 153–166 (1992), describe a number of methods to prepare drug loaded microspheres from PLGA polymers. PLGA-containing microspheres, however, have disadvantages which include the following. Firstly, the ability to manipulate the release of an encapsulated protein is limited because for most proteins, diffusion in PLGA matrices is negligible. The release of proteins from PLGA, therefore, depends upon the diffusion via pores present in the matrix and on the degradation or dissolution time of the microsphere. Also, during degradation of the PLGA, a low pH is generated in the polymeric matrix, which may be deleterious for many proteins.

In accordance with an aspect of the present invention, there is provided a composition for delivering a biologically active agent to a host. The composition comprises a product including the biologically active agent encapsulated in a matrix comprising a polyetherester copolymer.

The term "biologically active agent," as used herein, means an agent which provides a therapeutic or prophylactic effect. Such agents include, but are not limited to, antimicrobial agents (including antibacterial and anti-fungal agents), anti-viral agents, anti-tumor agents, hormones, and immunogenic agents.

In one embodiment, the polyetherester copolymer comprises a first component which is a polyalkylene glycol, and a second component which is a polyester formed from an alkylene glycol having from 2 to 8 carbon atoms and a dicarboxylic acid. The polyalkylene glycol, in one embodiment, is selected from the group consisting of polyethylene glycol, polypropylene glycol, and polybutylene glycol. In one embodiment, the polyalkylene glycol is polyethylene glycol.

In another embodiment, the polyester is selected from the group consisting of polyethylene terephthalate, polypropylene terephthalate, and polybutylene terephthalate. In a preferred embodiment, the polyester is polybutylene terephthalate.

In a preferred embodiment, the copolymer is a polyethylene glycol/polybutylene terephthalate block copolymer.

In another embodiment, the polyester has the following structural formula:

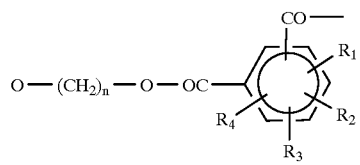

wherein n is from 2 to 8, and each of $R_1$, $R_2$, $R_3$, and $R_4$ is hydrogen, chlorine, nitro-, or alkoxy, and each of $R_1$, $R_2$, $R_3$, and $R_4$ is the same or different. Alternatively, the ester is derived from a binuclear aromatic diacid having the following structural formula:

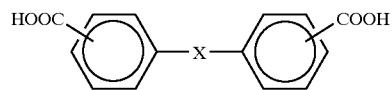

wherein X is —O—, —SO$_2$—, or —CH$_2$—.

Preferably, the ester has the following structural formula:

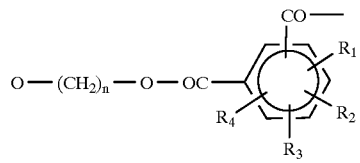

wherein n is from 2 to 8, and each of $R_1$, $R_2$, $R_3$, and $R_4$ is hydrogen, chlorine, nitro-, or alkoxy, and each of $R_1$, $R_2$, $R_3$, and $R_4$ is the same or different. More preferably, each of $R_1$, $R_2$, $R_3$, and $R_4$ is hydrogen.

In a preferred embodiment, the copolymer is a segmented thermoplastic biodegradable polymer comprising a plurality of recurring units of the first component and units of the second component. The first component comprises from about 30 wt. % to about 99 wt. %, based upon the weight of the copolymer, of units of the formula:

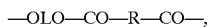

wherein L is a divalent radical remaining after removal of terminal hydroxyl groups from a poly(oxyalkylene)glycol.

The second component is present in an amount from about 1 wt. % to about 70 wt. %, based on the weight of the copolymer, and is comprised of units of the formula:

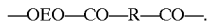

E is an organic radical selected from the group consisting of a substituted or unsubstituted alkylene radical having from 2 to 8 carbon atoms, and a substituted or unsubstituted ether moiety. R is a substituted or unsubstituted divalent radical remaining after removal of carboxyl groups from a dicarboxylic acid.

The poly(oxyalkylene)glycol, in one embodiment, may be selected from the group consisting of poly(oxyethylene) glycol, poly(oxypropylene)glycol, and poly(oxybutylene) glycol. Preferably, the poly(oxyalkylene)glycol is poly (oxyethylene)glycol.

The poly(oxyethylene)glycol may have a molecular weight of from about 200 to about 20,000. The exact molecular weight of the poly(oxyethylene)glycol is dependent upon a variety of factors, including the type of biologically active agent encapsulated by the matrix.

In one embodiment, E is a radical selected from the group consisting of a substituted or unsubstituted alkylene radical having from 2 to 8 carbon atoms, preferably having from 2 to 4 carbon atoms. Preferably, the second component is selected from the group consisting of polyethylene terephthalate, polypropylene terephthalate, and polybutylene terephthalate. In one embodiment, the second component is polybutylene terephthalate.

In a most preferred embodiment, the copolymer is a polyethylene glycol-polybutylene terephthalate copolymer.

In one embodiment, the polyethylene glycol/polybutylene terephthalate copolymer may be synthesized from a mixture of dimethylterephthalate, butanediol (in excess), polyethylene glycol, an antioxidant, and catalyst. The mixture is placed in a reaction vessel and heated to about 180° C., and methanol is distilled as transesterification occurs. During the transesterification, the ester bond with methyl is replaced with an ester bond with butyl. In this step the polyethylene glycol does not react. After transesterification, the temperature is raised slowly to about 245° C., and a vacuum (finally less than 0.1 mbar) is achieved. The excess butanediol is distilled and a prepolymer of butanediol terephthalate condenses with the polyethylene glycol to form a polyethylene glycol/polybutylene terephthalate copolymer. A terephthalate moiety connects the polyethylene glycol units to the polybutylene terephthalate units of the copolymer, and thus such copolymer also is sometimes hereinafter referred to as a polyethylene glycol terephthalate/polybutylene terephthalate copolymer, or PEGT/PBT copolymer. In another alternative, polyalkylene glycol/polyester copolymers may be prepared as described in U.S. Pat. No. 3,908,201.

It is to be understood, however, that the scope of the present invention is not to be limited to the specific copolymer hereinabove described, or to any particular means of synthesis.

Biologically active agents which may be contained in the polyetherester matrix, such as a polyethylene glycol terephthalate/polybutylene terephthalate matrix, include, but are not limited to, non-peptide, non-protein small-sized drugs having a molecular weight which in general is less than 500; and biologically active peptides or proteins.

Examples of non-peptide, non-protein small-sized drugs which may be contained in the polyetherester matrix such as a polyethylene glycol terephthalate/polybutylene terephthalate matrix, include, but are not limited to, the following:

1. Anti-tumor agents

| | |
|---|---|
| altretamin | fluorouracil |
| amsacrin | hydroxycarbamide |
| asparaginase | ifosfamid |
| bleomycin | lomustin |
| busulfan | melphalan |
| chlorambucil | mercaptopurin |
| chlormethin | methotrexate |
| cisplatin | mitomycin |
| cyclophosphamide | procarbazin |
| cytarabin | teniposid |
| dacarbazin | thiotepa |
| dactinomycin | tioguanin |
| daunorubicin | treosulphan |
| doxorubicin | tiophosphamide |
| estramucin | vinblastine |
| etoglucide | vincristine |
| etoposid | vindesin |

-continued

2. Antimicrobial agents 2.1 Antibiotics

Penicillins

| | |
|---|---|
| ampicillin | nafcillin |
| amoxicillin | oxacillin |
| azlocillin | penicillin G |
| carbenicillin | penicillin V |
| dicloxacillin | phenethicillin |
| floxacillin | piperacillin |
| mecillinam | sulbenicillin |
| methicillin | ticarcillin |
| mezlocitlin | |

Cephalosporins

| | |
|---|---|
| cefaclor | cephalothin |
| cefadroxil | cephapirin |
| cefamandole | cephradine |
| cefatrizine | cefsulodine |
| cefazolin | ceftazidim |
| ceforanide | ceftriaxon |
| cefoxitin | cefuroxime |
| cephacetrile | latamoxef |
| cephalexin | |

Aminoglycosides

| | |
|---|---|
| amikacin | neomycin |
| dibekacyn | kanamycin |
| gentamycin | netilmycin |
| kanamycin | tobramycin |

Macrolides

| | |
|---|---|
| amphotericin B | novobiocin |
| bacitracin | nystatin |
| clindamycin | polymyxins |
| colistin | rovamycin |
| erythromycin | spectinomycin |
| lincomycin | vancomycin |

Tetracyclines

| | |
|---|---|
| chlortetracycline | oxytetracycline |
| demeclocycline | rolitetracycline |
| doxycycline | tetracycline |
| minocycline | |

Other antibiotics

| | |
|---|---|
| chloramphenicol | rifamycin |
| rifampicin | thiamphenicol |

2.2 Chemotherapeutic agents

Sulfonamides

| | |
|---|---|
| sulfadiazine | sulfamethizol |
| sulfadimethoxin | sulfamethoxazole |
| sulfadimidin | sulfamethoxypyridazine |
| sulfafurazole | sulfaphenazol |
| sulfalen | sulfisomidin |
| sulfamerazine | sulfisoxazole |
| trimethoprim - sulfamethoxazole | |
| - sulfametrol | |

Urinary tract antiseptics

| | | |
|---|---|---|
| methenamine | quinolones: | norfloxacine |
| | | cinoxacine |
| nalidixic acid | nitro-compounds: | nitrofurantoine |
| | | nifurtoinol |
| oxolinic acid | | |

Anaerohic infections metronidazole

3. Drugs for tuberculosis

| | |
|---|---|
| aminosalicyclic acid | isoniazide |
| cycloserine | rifampicine |
| ethambutol | tiocarlide |
| ethionamide | viomycin |

4. Drugs for leprosy

| | |
|---|---|
| amithiozone | rifampicine | clofazimine  sodium sulfoxone
diaminodiphenylsulfone
(DDS, dapsone)

5. Antifungal agents amphotericin B  ketoconazole
clotrimazole  miconazole
econazole  natamycin
flucytosine  nystatine
griseofulvin

6. Antiviral agents aciclovir  idoxuridine
amantidine  methisazone
cytarabine  vidarabine
ganciclovir

7. Chemotherapy of amebiasis chloroquine  iodoquinol
clioquinol  metronidazole
dehydroemetine  paromomycin
diloxanide furoate  tinidazole
emetine

8. Anti-malarial agents chloroquine  pyrimethamine
hydroxychloroquine  quinine
mefloquine  sulfadoxine/pyrimeth.
 (Please provide complete
 term)
pentamidine  sodium suramin
primaquine  trimethoprim
proguanil

9. Anti-helminthiasis agents antimony potassium tartrate  niridazole
antimony sodium  oxamniquine
dimercaptosuccinate
bephenium  piperazine
dichlorophen  praziquantel
diethylcarbamazine  pyrantel pamoate
hycanthone  pyrivium pamoate
levamisole  stibophen
mebendazole  tetramisole
metrifonate  thiobendazole
niclosamide

10. Anti-inflammatory agents acetylsalicyclic acid  mefenamic acid
alclofenac  naproxen
azopropanone  niflumic acid
benzydamine  oxyphenbutazone
diclofenac  piroxicam
fenoprofen  pirprofen
flurbiprofen  sodium salicyclate
ibuprofen  sulindac
indomethacin  tiaprofenic acid
ketoprofen  tolmetin

11. Anti-gout agents colchicine  allopurinol

12. Centrally acting (opoid) analgesics alfentanil  methadone
bezitramide  morphine
buprenorf ine  nicomorphine
butorfanol  pentazocine
codeine  pethidine
dextromoramide  piritranide
dextropropoxyphene  sufentanil
fentanyl

13. Local anesthetics articaine  mepivacaine
bupivacaine  prilocaine
etidocaine  procaine
lidocaine  tetracaine

14. Drugs for Parkinson's disease amantidine  diphenhydramine
apomorphine  ethopropazine
benztropine mesylate  lergotril
biperiden  levodopa
bromocriptine  lisuride
carbidopa  metixen
chlorphenoxamine  orphenadrine
cycrimine  procyclidine
dexetimide  trihexyphenidyl

15. Centrally acting muscle relaxants baclofen  febarbamate
carisoprodol  mefenoxalone
chlormezanone  mephenesin
chlorzoxazone  metoxalone
cyclobenzaprine  methocarbamol
dantrolene  tolperisone
diazepam

16. Hormones and hormone antagonists

16.1 Corticosteroids

16.1.1 Mineralocorticosteroids cortisol
desoxycort icosterone
fluorhydrocortisone

16.1.2 Glucocorticosteroids beclomethasone  flurandrenolide
betamethasone  halcinonide
cortisone  hydrocortisone
dexamethasone  medrysone
fluocinolone  methylprednisolone
fluocinonide  paramethasone
fluocortolone  prednisolone
fluorometholone  prednisone
fluprednisolone  triamcilone (acetonide)

16.2 Androgens

16.2.1 Androgenic steroids used in therapy danazole  methyltestosterone
fluoxymesterone  testosterone and salts
 thereof
mesterolone

16.2.2 Anabolic steroids used in therapy calusterone  nandrolone and salts
 thereof
dromos tanolone  oxandrolone
ethylestrenol  oxymetholone
methandriol  stanozolol
methandrostenolone  testolactone

16.2.3 Antiandrogens cyproterone acetate

16.3 Estrogens

16.3.1 Estrogenic steroids used in therapy diethylstilbestrol  ethinylestradiol
estradiol  mestranol
estriol  quinestrol

16.3.2 Anti-estrogens chlorotrianisene  nafoxidine
clomiphene  tamoxifen
ethamoxytriphetol

16.4 Progestins allylestrenol  levonorgestrel
desogestrel  lynestrenol
dimethisterone  medroxyprogesterone
dydrogesterone  megestrol acetate
ethinylestrenol  norethindrone
ethisterone  norethisterone
ethynadiol diacetate  norethynodrel
etynodiol  norgestrel
hydroxyproges terone  proge sterone

-continued

17. Thyroid drugs 17.1 Thyroid drugs used in therapy levothyronine                liothyronine 17.2 Anti-thyroid drugs used in therapy carbimazole                methylthiouracil
methimazole                propylthiouracil When a small-sized drug, such as those hereinabove described, is contained in a polyethylene glycol terephthalate/polybutylene terephthalate matrix, the polyethylene glycol component of the copolymer preferably has a molecular weight of from about 200 to about 400. Also, the polyethylene glycol terephthalate is present in the copolymer in an amount of from about 30 wt. % to about 80 wt. % of the weight of the copolymer, preferably from about 50 wt. % to about 60 wt. % of the weight of the copolymer. In general, the polybutylene terephthalate is present in the copolymer in an amount of from about 20 wt. % to about 70 wt. % of the copolymer, preferably in an amount of from about 40 wt. % to about 50 wt. % of the copolymer.

When the polyetherester matrix, such as a polyethylene glycol terephthalate/polybutylene terephthalate matrix, contains a hydrophobic small-sized drug, such as, for example, a steroid hormone, the matrix also may include at least one hydrophobic antioxidant. Hydrophobic antioxidants which may be employed include, but are not limited to, tocopherols, such as α-tocopherol, β-tocopherol, γ-tocopherol, Δ-tocopherol, epsilon-tocopherol, $zeta_1$-tocopherol, $zeta_2$-tocopherol, and eta-tocopherol; and 1-ascorbic acid 6-palmitate. Such hydrophobic antioxidants retard the degradation of the polyetherester copolymer matrix, and retard the release of the biologically active agent contained in the matrix. Thus, the use of a hydrophobic or lipophilic antioxidant is applicable particularly to the formation of microspheres which include drugs which tend to be released quickly from the microspheres, such as, for example, small drug molecules having a molecular weight less than 500.

The at least one hydrophobic antioxidant may be present in the matrix in an amount of from about 0.1 wt. % to about 10 wt. % of the total weight of the matrix, preferably from about 0.5 wt. % to about 2 wt. %.

When the matrix includes a hydrophilic small-sized drug, such as an aminoglycoside, the matrix may also include, in addition to the at least one hydrophobic antioxidant hereinabove described, a hydrophobic molecule such as cholesterol, ergosterol, lithocholic acid, cholic acid, dinosterol, betuline, or oleanolic acid may be employed in order to retard the release rate of the agent from the polyetherester copolymer matrix. Such hydrophobic molecules prevent water penetration into the matrix, but do not compromise the degradability of the matrix. In addition, such molecules have melting points from 150° C. to 200° C. or more. Therefore, a small percentage of these molecules increases the glass transition temperature of the matrix, which decreases the matrix diffusion coefficient for the biologically active agent, such as a small drug molecule, to be released. Thus, such hydrophobic molecules provide for a more sustained release of a biologically active agent from the matrix.

The at least one hydrophobic molecule may be present in the matrix in an amount of from about 0.1 wt. % to about 20 wt. %, preferably from about 1.0 wt. % to about 5.0 wt. %.

If it is desired to increase the hydrophilicity of the polymer, and thereby increase the degradation rate and drug releasing rate of the copolymer, the PEGT/PBT copolymer may be modified by replacing partially the terephthalate with succinate and/or by replacing partially the butylene with dioxyethylene.

In one embodiment, terephthalate is replaced by succinate in an amount of from about 0.1 mole % to about 20 mole %, preferably from about 0.1 mole % to about 5 mole %, by replacing dimethylterephthalate as a starting component with dimethylsuccinate.

In another embodiment, butylene is replaced with diethyleneglycol in an amount of from about 0.1 mole % to about 20 mole %, preferably from about 0.5 mole % to about 2 mole %, by replacing 1,4-butanediol as a starting component.

In yet another embodiment, terephthalate is replaced with succinate, and butylene is replaced with diethyleneglycol in the amounts and according to the methods hereinabove described.

Examples of peptides or proteins which may be contained in the matrix include, but are not limited to, immunogenic peptides or immunogenic proteins, which include, but are not limited to, the following:

Toxins
diphtheria toxin
tetanus toxin
Viral Surface Antigens or Parts of Viruses
adenoviruses
Epstein-Barr Virus
Hepatitis A Virus
Hepatitis B Virus
Herpes viruses
HIV-1
HIV-2
HTLV-III
Influenza viruses
Japanese encephalitis virus
Measles virus
Papilloma viruses
Paramyxoviruses
Polio Virus
Rabies Virus
Rubella Virus
Vaccinia (Smallpox) viruses
Yellow Fever Virus
Bacterial Surface Antigens or Parts of Bacteria
*Bordetella pertussis*
*Campylobacter pylori*
(*Helicobacter pylori*)
*Clostridium tetani*
*Corynebacterium diphtheria*
*Escherichia coli*
*Haemophilus influenza*
Klebsiella species
*Legionella pneumophila*
*Mycobacterium bovis*
*Mycobacterium leprae*
*Mycobacterium tuberculosis*
*Neisseria gonorrhoeae*
*Neisseria meningitidis*
Proteus species
*Pseudomonas aeruginosa*
Salmonella species
Shigella species
*Staphylococcus aureus*
*Streptococcus pyogenes*
*Vibrio cholera*
*Yersinia pestis*

(*Pasteurella pestis*)
Surface Antigens of Parasites Causing Disease or Portions of Parasites
*Plasmodium vivax*—malaria
*Plasmodium falciparum*—malaria
*Plasmodium ovale*—malaria
*Plasmodium malariae*—malaria
*Leishmania tropica*—leishmaniasis
*Leishmania donovani*—leishmaniasis
*Leishmania branziliensis*—leishmaniasis
*Trypanosoma rhodescense*—sleeping sickness
*Trypanosoma gambiense*—sleeping sickness
*Trypanosoma cruzi*—Chagas' disease
*Schistosoma mansoni*—schistosomiasis
*Schistosoma haematobium*—schistosomiasis
*Schistosoma japonicum*—schistosomiasis
*Trichinella spiralis*—trichinosis
*Stronglyloides duodenale*—hookworm
*Ancyclostoma duodenale*—hookworm
*Necator americanus*—hookworm
*Wucheria bancrofti*—filariasis
*Brugia malaya*—filariasis
*Loa loa*—filariasis
*Dipetalonema perstaris*—filariasis
*Dracuncula medinensis*—filariasis
*Onchocerca volvulus*—filariasis
Immunoglobulins
Ig G
Ig A
Ig M
Antirabies immunoglobulin
Antivaccinia immunoglobulin
Antitoxins
Botulinum antitoxin
diphtheria antitoxin
gas gangrene antitoxin
tetanus antitoxin Other peptides or proteins which may be encapsulated include, but are not limited to, antigens which elicit an immune response against Foot and Mouth Disease, hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors; fibrinolytic enzymes, such as urokinase, kidney plasminogen activator; and clotting factors, such as Protein C, Factor VIII, Factor IX, Factor VII, and Antithrombin III. Examples of other proteins or peptides which may be encapsulated include, but are not limited to, albumin, atrial natriuretic factor, renin, superoxide dismutase, $\alpha_1$-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-$\alpha$-endorphin, gonadotropin releasing hormone, leuprolide, $\alpha$-MSH, and metkephamid. It is to be understood, however, that the scope of the present invention is not to be limited to any specific peptides or proteins.

When a protein having a molecular weight of greater than 10,000 is contained in the polyethylene glycol terephthalate/polybutylene terephthalate matrix, the polyethylene glycol component of the copolymer may have a molecular weight of from about 1,000 to about 20,000. The polyethylene glycol terephthalate may be present in the copolymer in an amount of from about 30 wt. % to about 90 wt. % of the weight of the copolymer, preferably from about 60 wt. % to about 70 wt. %. The polybutylene terephthalate may be present in the copolymer in an amount of from about 10 wt. % to about 70 wt. % of the weight of the copolymer, preferably from about 30 wt. % to about 40 wt. %.

When the polyetherester matrix, such as a polyethylene glycol terephthalate/polybutylene terephthalate matrix, contains a protein, the matrix may also include a hydrophilic antioxidant. Examples of hydrophilic antioxidants include, but are not limited to, those having the following structural formula:

$$(X_1)_Y\text{-A-}(X_2)_Z$$

Each of Y and Z is 0 or 1, wherein at least one of Y and Z is 1. Each of $X_1$ and $X_2$ is selected from the group consisting of:

and

Each $R_1$ is hydrogen or an alkyl group having 1 to 4 carbon atoms, preferably methyl, and each $R_1$ is the same or different. $R_2$ is hydrogen or an alkyl group having 1 to 4 carbon atoms, preferably methyl. Q is NH or oxygen. Each of $X_1$ and $X_2$ may be the same or different.

A is:

$$-(-R_3-O-)_n-R_4$$

$R_3$ is an alkyl group having 1 or 2 carbon atoms, preferably 2 carbon atoms. n is from 1 to 100, preferably from 4 to 22. $R_4$ is an alkyl group having from 1 to 4 carbon atoms, preferably 1 or 2 carbon atoms.

In one embodiment, one of Y and Z is 1, and the other of Y and Z is 0. In another embodiment, each of Y and Z is 1.

In yet another embodiment, $R_3$ is ethyl.

In a further embodiment, $R_4$ is methyl or ethyl.

In a preferred embodiment, $R_1$ is methyl, $R_2$ is methyl, $R_3$ is ethyl, $R_4$ is methyl, one of Y and Z is 1 and the other of Y and Z is 0, Q is NH, n is 21 or 22, and the antioxidant has the following structural formula:

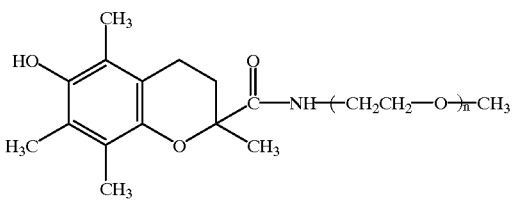

In another embodiment the hydrophilic antioxidant has the following structural formula:

Each of Y and Z is 0 or 1, wherein at least one of Y and Z is 1. Each of $X_3$ and $X_4$ is:

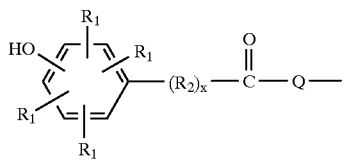

Each $R_1$ is hydrogen or an alkyl group having 1 to 4 carbon atoms, $R_2$ is an alkyl group having 1 to 4 carbon atoms, x is 0 or 1, and Q is NH or oxygen. Each $R_1$ is the same or different, and each of the $X_3$ and $X_4$ is the same or different.

A is:

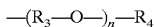

$R_3$ is an alkyl group having 1 or 2 carbon atoms, preferably 2 carbon atoms. n is from 1 to 100, preferably from 4 to 22. $R_4$ is an alkyl group having from 1 to 4 carbon atoms, preferably 1 or 2 carbon atoms.

In one embodiment, at least one, preferably two, of the $R_1$ moieties is a tert-butyl moiety. When two of the $R_1$ moieties are tert-butyl moieties, each tert-butyl moiety preferably is adjacent to the —OH group.

The at least one hydrophilic antioxidant may be present in the matrix in an amount of from about 0.1 wt. % to about 10 wt. % of the total weight of the matrix, preferably from about 1.0 wt. % to about 5.0 wt. %.

The hydrophilic antioxidants in general provide for an increased degradation rate of the polyetherester copolymer. The increased degradation of the polyetherester copolymer, however, is not accompanied by an increase in acid formation. Thus, the use of such hydrophilic antioxidants in the matrix is applicable particularly to the encapsulation of peptide or protein molecules by the matrix. Thus, when the protein or peptide molecule is released from the matrix upon the degradation thereof, the protein will not be denatured by acid degradation products. Therefore, a hydrophilic antioxidant may be employed in order to provide for an increased rate of release of peptide or protein molecule from the matrix while avoiding denaturation of the peptide or protein.

Also, the degradation rate of the PEGT/PBT copolymer may be increased, if desired, by replacing partially the terephthalate with succinate and/or by replacing partially the butylene with dioxyethylene in the amounts hereinabove described.

If one wishes to increase the diffusion rate of the protein having a molecular weight greater than 10,000 through the PEGT/PBT copolymer, one may add polyethylene glycol having a molecular weight of from about 4,000 to about 10,000 to the PEGT/PBT copolymer. Such polyethylene glycol may be present in an amount of up to about 10 wt. %, based on the weight of the PEGT/PBT copolymer.

In addition, the diffusion rate of the protein may be increased by increasing the weight of the polyethylene glycol component of the PEGT/PBT copolymer. For example, when the polyethylene glycol component of the PEGT/PBT copolymer has a molecular weight of from about 6,000 to about 20,000, hydrophilic pores may be formed in the matrix, such pores providing an increased diffusion rate.

When the PEGT/PBT matrix includes a peptide or protein having a molecular weight less than 10,000, the polyethylene glycol preferably has a molecular weight of from about 200 to about 6,000. The polyethylene glycol terephthalate may be present in the copolymer in an amount of from about 30 wt. % to about 80 wt. %, based on the weight of the copolymer. The polybutylene terephthalate may be present in the copolymer in an amount of from about 20 wt. % to about 70 wt. %, based on the weight of the copolymer.

The PEGT/PBT matrix may include a hydrophobic antioxidant, hydrophobic molecule, and/or a hydrophilic antioxidant in the amounts hereinabove described. The type and exact amount of antioxidant or hydrophobic molecule employed is dependent upon the molecular weight of the protein. If the PEGT/PBT matrix copolymer includes a peptide having a low molecular weight (such as, for example, less than 500), the PEGT/PBT copolymer may include a hydrophobic antioxidant and/or hydrophobic molecule as hereinabove described. If the PEGT/PBT copolymer matrix contains a large peptide or protein (such as, for example, insulin), the matrix also may include a hydrophilic antioxidant such as those hereinabove described and in the amounts hereinabove described, and may also include polyethylene glycol having a molecular weight from about 1,000 to about 4,000, in an amount of from about 1 wt. % to about 10 wt. %, based on the weight of the copolymer.

If desired, the degradation rate of the PEGT/PBT copolymer may be increased by replacing partially the terephthalate with succinate and/or by replacing partially the butylene with dioxyethylene, in amounts hereinabove described.

The polyetherester copolymer, such as a PEGT/PBT copolymer, with or without the at least one antioxidant, or hydrophobic molecule, or polyethylene glycol, is formed into microspheres which contain a biologically active agent, such as a drug or a protein as hereinabove described. In general, microspheres are fine spherical particles having a diameter up to 1,000µ, and containing a biologically active agent. The microsphere may be a homogeneous or monolithic microsphere in which the biologically active agent is dissolved or dispersed throughout the polymer matrix. In another embodiment, the microsphere may be of a reservoir type in which the biologically active agent is surrounded by the polymer in the mononuclear or polynuclear state. In another embodiment, when the biologically active agent is a small hydrophilic drug, the drug may first be dispersed in a hydrophobic or lipophilic excipient, which combination then is dispersed in the form of particles, droplets, or microsuspensions in the polyetherester matrix. Microspheres then can be formed from the emulsion.

The microspheres may be prepared by techniques known to those skilled in the art, including but not limited to, solvent evaporation and spray drying techniques.

In one embodiment, a solvent evaporation technique, the polyetherester is placed in an organic solvent such as methylene chloride, and polyvinyl alcohol is employed as an emulsifying agent. The mean particle diameter and the particle size depend upon the viscosity or concentration of the aqueous polyvinyl alcohol phase. Other parameters, such as the concentration of the polyetherester solution and the stirring rate, have a minor effect on the particle size and distribution. The concentration of the polyetherester solution determines the porosity of the microspheres. At higher polyetherester concentrations, such as, for example, about 20%, dense and smooth microspheres are obtained. At lower concentrations of polyetherester, such as, for example, about 5%, porous microspheres are obtained.

When the microspheres are formed by a spray drying process, a low concentration of polyetherester copolymer, from about 0.5% to about 5.0%, preferably about 2%, in the organic solvent, such as methylene chloride, is employed. Spray drying results in general in the production of porous, irregularly shaped particles.

As the microspheres are being formed, a biologically active agent is encapsulated in the microspheres or microparticles. In general, when the solvent evaporation technique is employed, an aqueous solution of the agent first is emulsified in a solution of the polyetherester in an organic solvent such as methylene chloride. The emulsion then subsequently is emulsified in an aqueous solution of polyvinyl alcohol, which yields a water-in-oil-in-water emulsion. The organic solvent, such as methylene chloride, then is evaporated to yield the microspheres. When the spray drying technique is employed, an aqueous solution of the agent is emulsified in a solution of the polyetherester in an organic solvent such as methylene chloride, as hereinabove described. The water-in-oil emulsion then is spray-dried using a spray dryer.

The microspheres may be administered by a variety of means known to those skilled in the art, including parenteral and mucosal administration, such as oral administration (such as, for example, buccal administration), subcutaneous administration, intravenous administration, intraarterial administration, intraperitoneal administration intramuscular administration, vaginal administration, and rectal administration. The microspheres also may be administered topically. The polyetherester microspheres are compatible with a wide variety of biologically active agents, and thus prevent denaturation of such agents until such agents are delivered to a desired cell, tissue, or organ. Examples of pharmaceutical carriers which may be employed include, but are not limited to, gels, including hyaluronic acid gels and macromolecular polysaccharide gels, creams, and ointments.

For example, the microspheres may be contained in a gel, cream, or ointment, and may, if desired, be covered by a barrier, when administered topically. Thus, the microspheres may contain one or more biologically active agents employed in the treatment of skin diseases, such as psoriasis, eczema, seborrhea, and dermatitis.

In another embodiment, the microspheres may be contained in a gel such as a hyaluronic acid gel or a macromolecular polysaccharide gel. Such an embodiment is applicable particularly to parenteral applications, such as during and after surgery.

When administered by injection, the microspheres may be contained in a pharmaceutical carrier such as water, saline solution (for example, 0.9% saline), or a solution containing a surfactant in an amount of from about 0.1% wt./vol. to about 0.5% wt./vol. Examples of surfactants which may be employed include, but are not limited to, Tween 80 surfactant.

In another embodiment, the microspheres may be contained in a capsule coated with a gastric protective layer, such as, for example, Eudragit® methacrylate copolymers.

In general, the microspheres have a size of up to 1,000 microns, preferably from about 1 micron to about 500 microns. The size of the microspheres may be dependent upon a variety of factors, including but not limited to, the method of forming the microspheres and the route of administration of the microspheres after their formation.

When administered orally, the microspheres in general have a size from about 0.1 micron to about 1,000 microns. When one desires to deliver the microspheres to the Peyer's patches, the microspheres may have a diameter of from about 1 micron to about 10 microns, more preferably from about 1 micron to about 5 microns. The polyetherester copolymer protects the biologically active agent by preventing denaturation of the biologically active agent until the biologically active agent reaches the desired cell, tissue, or organ.

For example, this embodiment is applicable particularly to the oral delivery of peptide or protein molecules (including immunogenic peptides or proteins), whereby the microspheres including the peptide or protein travel through the gastrointestinal tract for delivery to the Peyer's patches located in the ileum or lower part of the intestine. Peptides and proteins, however, are highly susceptible to degradation or denaturation in the gastrointestinal tract. The polyetherester copolymer, which is compatible with peptide and protein molecules, protects the peptide or protein from degradation or denaturation in the gastrointestinal tract until the microspheres deliver the peptide or protein to the Peyer's patches. Thus, the microspheres of the present invention may be employed as part of a pharmaceutical composition for oral administration of biologically active peptides or proteins to the Peyer's patches.

In one embodiment, the microspheres may include an immunogenic peptide or protein and thus may be employed in an orally administered vaccine. The polyetherester copolymer protects the immunogenic protein or peptide as it travels through the gastrointestinal tract, until the microspheres deliver the immunogenic protein or peptide to the Peyer's patches. Once the immunogenic peptide or protein is delivered to the Peyer's patches, an immune response is generated against the peptide or protein.

When administered via injection, the microspheres have a size of from about 1 micron to about 30 microns, preferably from about 10 microns to about 20 microns. Such microspheres, when administered in combination with an acceptable pharmaceutical carrier, may be employed in the treatment of a variety of diseases or disorders, depending upon the biologically active material which is encapsulated. Thus, injectable formulations including the microspheres of the present invention may be employed in the treatment of locally confined diseases such as arthritis, rheumatism, inflammations, local pain processes, local infections, local skin diseases, tumors (or their sites after surgical removal as a post-operative treatment to destroy any tumor cells possibly remaining), and local brain diseases (e.g., Parkinson's disease). Such injectable formulations also may be employed in long-term therapeutic treatments, such as, for example, treatments with corticosteroids, androgens, anti-androgens, estrogens, anti-estrogens, progestangenic agents or thyroid hormones, or with anti-tuberculosis, anti-leprosy, or anti-malaria drugs.

BRIEF DESCRIPTION OF THE DRAWINGS

The invention will be described with respect to the drawings, wherein:

FIG. 8 is a graph showing the release of diphtheria toxoid from PEGT/PBT 80/20 microspheres over a period of almost 600 days;

FIG. 9 is a graph showing the release of lysozyme from PolyActive 80/20 microspheres;

Figure 1:
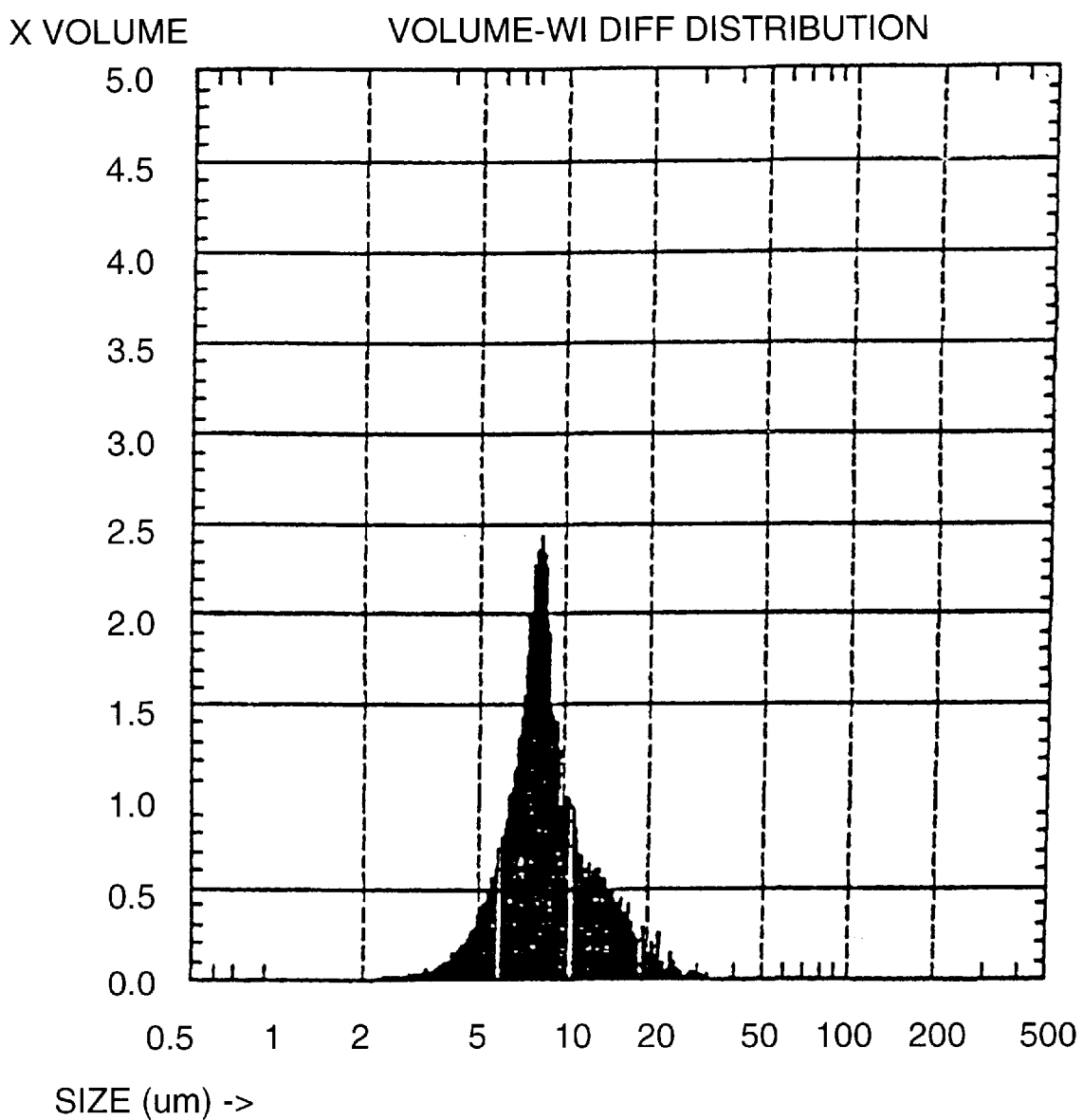
FIG. 1 is a graph showing size distribution of microspheres prepared by a solvent evaporation technique.

The invention now will be described with respect to the following examples; however, the scope of the present invention is not intended to be limited thereby.

EXAMPLE 1

In this example, poly(ethylene oxide)terephthalate/poly (1,4-butylene)terephthalate (PEGT/PBT) copolymers were synthesized, wherein such copolymers had PEGT/PBT weight ratios of 80/20, 70/30, and 60/40. Such copolymers also are sometimes hereinafter referred to as PolyActive, or PA. The polyethylene glycol component of the PA 70/30 and PA 60/40 copolymers had a molecular weight of 1,000. For the PA 80/20 copolymers, batches having a polyethylene glycol component with molecular weights of 1,000, 2,000, and 4,000 were prepared.

Diphtheria toxoid (Mw 62,000) was obtained from the Netherlands National Institute of Public Health and Environmental Protection, Bilthoven, The Netherlands (2025 LF/ml; 1 LF corresponds to about 4 μg protein). The term "LF" means limes flocculation, the International Unit for vaccines.

Polyvinyl alcohol (PVA, 87–89% hydrolysed; Mw 13,000–23,000) was obtained from Aldrich, Belgium. Bovine serum albumin (BSA, fraction V) was obtained from Acros, Geel, Belgium. Lysozyme (chick egg white) was obtained from Sigma and IgG (immunoglobulin G, fraction II) was from ICN Biomedicals, Zoetermeer, The Netherlands.

Poly(DL-Lactide/glycolide) 50/50 w/w (batch number DL260AM), intrinsic viscosity 0.58 dl/g, $M_w$ relative to polystyrene was 50 kD, was obtained from Purac, Gorinchem, The Netherlands. This polymer is sometimes hereinafter referred to as "PLGA."

Preparation of PEGT/PBT Microspheres

For preparation of the PEGT/PBT microspheres, two methods were used, namely, the solvent evaporation method and the spray-drying method. The preparation of PEGT/PBT microspheres using the solvent evaporation method was based on protocols used to prepare PLGA microspheres as disclosed in O'Hagan, et al., *Intern. J. Pharmaceutics*, Vol. 1033, pgs 37–45 (1994). In general, PEGT/PBT was dissolved in 20 ml $CH_2Cl_2$ (concentration ranging from 5–20% (w/v)). This solution was added to an aqueous solution of PVA (concentration 1–10%) After stirring (mechanical stirrer, 1200 rpm) an oil-in-water emulsion was formed. Due to the evaporation of the $CH_2Cl_2$, PEGT/PBT precipitated from the solution to yield microspheres. After two hours (the time necessary for almost complete evaporation of the $CH_2Cl_2$), the formed PEGT/PBT microspheres were collected by centrifugation, washed with water (3 times) and finally air dried.

For the preparation of protein loaded microspheres, first a water-in-oil emulsion was created. The protein was dissolved in water to a concentration of about 170 mg/ml for BSA, 100 mg/ml for lysozyme and 2025 LF/ml for diphtheria toxoid and 0.5 ml of the protein solution was added to 20 ml of PolyActive in $CH_2Cl_2$. This mixture was homogenized using an Ultraturrax (Type 18/10, emulsification time: 10 seconds), yielding a water-in-oil emulsion which was added to 200 ml of an aqueous PVA solution and further treated as described above.

For the preparation of PEGT/PBT microspheres using the spray drying method, the polymer was dissolved in a suitable volatile organic solvent (1 gram PolyActive dissolved in 50 ml $CH_2Cl_2$). This solution was spray dried using a laboratory Buchi Spray Dryer at an inlet temperature of 42° C.; an outlet temperature of 38° C.; and a flow rate of 5 ml/min.

For the preparation of protein loaded microspheres, first a water-in-oil emulsion was formed as described hereinabove with respect to the solvent evaporation technique which was spray dried as described above.

Preparation of PLGA Microspheres

PLGA microspheres were obtained by the solvent evaporation technique and the spray drying technique as described for the PEGT/PBT microspheres.

Microsphere Characterization

The particle size (number weight and volume weight) and the particle size distribution were determined by a laser light blocking technique (Accusizer®, model 770, Particle Sizing Systems, Santa Barbara, Calif., U.S.A). The shape and the surface characteristics (porosity) of the microspheres were established by scanning electron microscopy analysis.

Protein Determinations

The protein concentrations (BSA, lysozyme) of the samples was measured with the Biorad protein assay using the micro assay procedure described in Bradford, *Anal.Biochem.*, Vol. 72, pgs. 248–254 (1976). Diphtheria toxoid was determined using an enzyme-linked immunosorbent assay (ELISA).

Molecular Weight Determinations

Molecular weights ($M_n$ and $M_w$) of PEGT/PBT and PLGA were determined by gel permeation chromatography (GPC). For PLGA, Shodex columns were used and $CHCl_3$ was the mobile phase. The columns were calibrated using polystyrene standards of known molecular weights.

Determination of α-Tocopherol Content of the Microspheres

The PEGT/PBT materials hereinabove described also contain 0.5% of a suitable antioxidant (α-tocopherol). The amount of antioxidant present after the preparation of the microspheres was determined using HPLC analysis.

Protein Encapsulation Efficiency

Bovine serum albumin (BSA) encapsulation efficiency was determined by dissolving an aliquot of the protein loaded microspheres (±25 mg) in $CH_2Cl_2$ (0.5 ml). This solution was extracted 5 to 10 times with water (0.5 ml). The protein concentration in the extracts was determined using the Biorad assay. From the extracted amount of protein, the encapsulation efficiency was calculated. As a control, the protein concentration of the polyvinyl alcohol and the washing solutions also were determined.

Encapsulation efficiency of diphtheria toxoid was determined by determining the amount of protein in the polyvinyl alcohol solution and the different washing solutions.

In Vitro Release of Proteins from Microspheres

A known weight of the microspheres (±100 mg) was placed into an Eppendorf tube and a 1 ml buffer (PBS containing 0.02% $NaN_3$) was added. The tubes were closed and rotated at 37° C. At selected time intervals the microspheres were centrifuged, the supernatant removed, the pellet resuspended in 1 ml buffer and centrifuged again. The supernatant was added to the first supernatant and the concentration of the protein in the pooled sample was determined using the Biorad protein assay.

Aging of the PEGT/PBT and the PLGA Microspheres

PEGT/PBT and the PLGA microspheres were aged at 37° C. and at 0% and 100% humidity, respectively. The molecular weights of the polymers were determined by GPC and were established as a function of the aging time.

Results

Microsphere Preparation via the Solvent Evaporation Technique 33 batches of PolyActive (PEGT/PBT or PA) and PLGA microspheres were prepared via the solvent evaporation technique. The characteristics of such batches of microspheres are given in Table I below.

TABLE I

Characteristics of Polyactive (PA)/PLGA microspheres prepared by solvent evaporation technique

| batch no. | polymer; concentration % (w/v) | PVA (%) | Yield (%) | protein and encapsulation efficiency | Size (μm) number wght | Size (μm) volume wght |
|---|---|---|---|---|---|---|
| 1 | PA 80/20; 5% | 1 | 65 | DT; 2% | 13 | 37 |
| 2 | PA 80/20; 10% | 1 | 83 | DT; 24% | 13 | 88 |
| 3 | PA 80/20; 20% | 1 | 78 | DT; 30% | 13 | 101 |
| 4 | PA 70/30; 5% | 1 | 77 | NA | 14 | 38 |
| 5 | PA 70/30; 5% | 5 | 81 | NA | 12 | 25 |
| 6 | PA 70/30; 5% | 10 | 82 | NA | 6 | 9 |
| 7 | PA 70/30; 10% | 1 | 77 | NA | 15 | 112 |
| 8 | PA 70/30; 10% | 5 | 85 | NA | 8 | 47 |
| 9 | PA 70/30; 10% | 5 | 88 | NA | 8 | 41 |
| 10 | PA 70/30; 10% | 5 | 85 | NA | 8 | 38 |
| 11 | PA 70/30; 20% | 1 | 80 | NA | 13 | 456 |
| 12 | PA 70/30; 20% | 5 | 82 | NA | 13 | 36 |
| 13 | PA 70/30; 20% | 10 | 74 | NA | 9 | 21 |
| 14 | PA 60/40; 5% | 1 | 78 | NA | 14 | 48 |
| 15 | PA 60/40; 10% | 1 | 60 | NA | 19 | 144 |
| 16 | PA 70/30; 5% | 1 | 78 | BSA; 104% | 14 | 57 |
| 17 | PA 70/30; 10% | 1 | 78 | BSA; 115% | 9 | 65 |
| 18 | PA 70/30; 20% | 1 | 54 | BSA; 75% | 19 | 369 |
| 19 | PA 60/40; 5% | 1 | 80 | BSA; 93% | 11 | 43 |
| 20 | PA 60/40; 10% | 1 | 53 | BSA; 55% | 17 | 444 |
| 21 | PLGA 5% | 1 | 83 | BSA; 82% | 8 | 29 |
| 22 | PLGA 10% | 1 | 77 | BSA; 85% | 11 | 71 |
| 23 | PA 70/30; 5% | 5 | 84 | DT; 85% | 5 | 21 |
| 24 | PA 70/30; 10% | 5 | 72 | DT; 94% | 9 | 70 |
| 25 | PA 70/30; 20% | 5 | 66 | DT; 88% | 12 | 202 |
| 26 | PA 70/30; 20% | 5 | 51 | DT; 98% | 9 | 145 |
| 27 | PA 60/40; 5% | 5 | 88 | DT; 94% | 6 | 28 |
| 28 | PA 60/40; 10% | 5 | 64 | DT; 10% | 13 | 51 |
| 29 | PLGA 5% | 5 | 78 | DT; 98% | 7 | 16 |
| 30 | PLGA 10% | 5 | 84 | DT; 27% | 8 | 41 |
| 31 | PA 80/20; 5% (PEG 1000) | 1 | 62 | lys | 15 | 52 |
| 32 | PA 80/20; 5% (PEG 2000) | 1 | 70 | lys | 20 | 80 |
| 33 | PA 80/20; 5% (PEG 4000) | 1 | 77 | lys | 22 | 89 |

The microsphere yield (defined as the mass of the microspheres/mass of polymer used for the preparation of microspheres) was normally about 80%. FIG. 1 gives a representative example of the particle size distribution of the obtained microspheres (Batch 6, PA 70/30, 5% in $CH_2Cl_2$, 10% PVA) as determined using the Accusizer.

The obtained size distribution is rather normal for microspheres prepared via the solvent evaporation technique. The batch shown in FIG. 1 has a number weight mean of 6.0 μm and a volume weight mean of 9.4 μm; 95% of the particles has a diameter between 5 and 17 μm.

Figure 2:
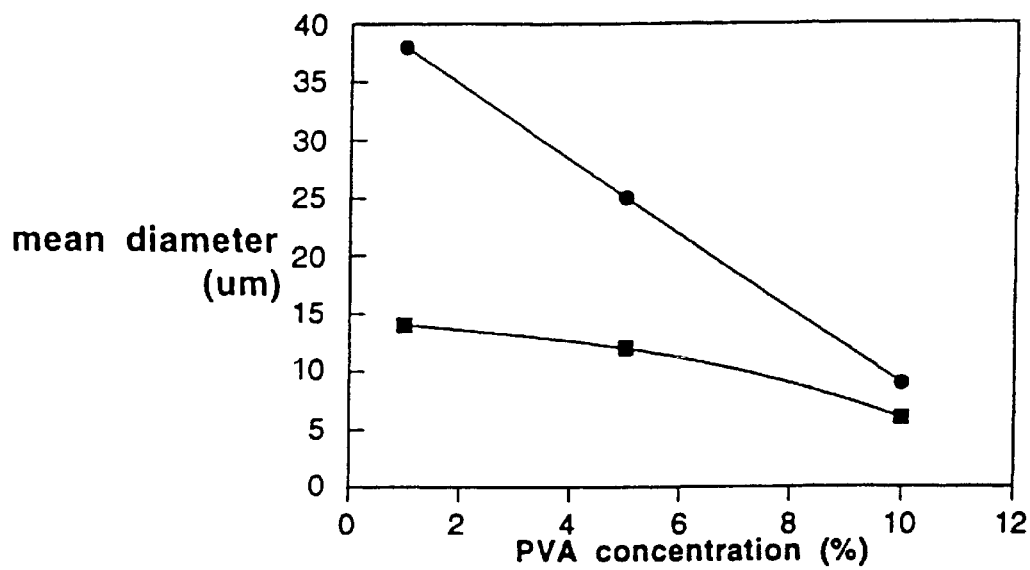
FIG. 2 is a graph showing the effect of PVA on the size distribution of 70/30 PEGT/PBT microspheres.

The effect of the PEGT/PBT concentration and the PVA concentration on particle size distribution was investigated. FIG. 2 shows the effect of the PVA concentration on the size (distribution) of the 70/30 PEGT/PBT microspheres. From this figure it can be seen that an increasing PVA concentration yielded smaller particles with a smaller distribution. A higher viscosity (due to higher PVA concentration) of the external phase will yield smaller droplets of emulsified polymer and finally, after evaporation of the solvent, smaller sized PEGT/PBT particles. Interestingly, a higher concentration of PVA also yielded a more narrow particle size distribution (ratio of volume weight average and number weight average becomes smaller at higher PVA concentration).

Figure 3:
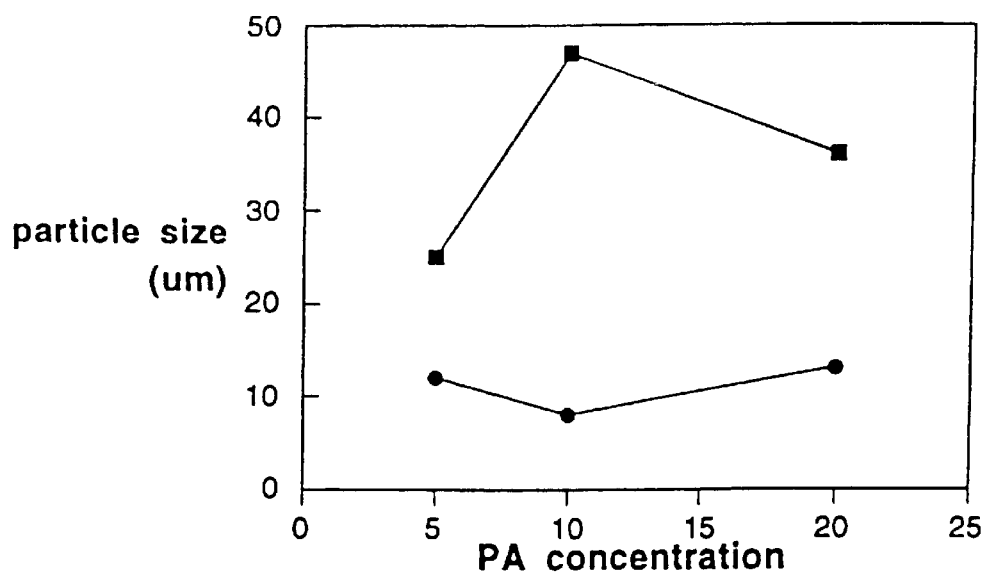
FIG. 3 is a graph showing the effect of 70/30 PEGT/PBT concentration on particle size distribution.

Whereas PVA has a substantial effect on the particle size, the effect of the 70/30 PEGT/PBT concentration on particle size and particle size distribution is less pronounced (FIG. 3). In addition, no large effect of the stirring rate on the particle size was observed.

It can be concluded that the best way to control and tailor the particle size of PEGT/PBT microspheres is the PVA concentration of the external phase.

By GPC measurements it was shown that the molecular weight of PEGT/PBT of the obtained microspheres was not significantly different from the polymer used for the preparation of the microspheres. This demonstrates that during the preparation, washing, and drying, no degradation (hydrolysis) of the polymer occurs.

The amount of antioxidant in two different microsphere batches was determined (Batch 7 (PEGT/PBT 70/30) and Batch 14 (PEGT/PBT 60/40)). No decrease in α-tocopherol was observed, which can be ascribed to the very low solubility of this compound in water. The antioxidant might inhibit the oxidative degradation of PA during in vitro release studies with hydrolysis being the dominant degradation route.

Also prepared by the solvent evaporation technique described hereinabove were the following microspheres:
Microsphere A
 (i) 89 wt. % of a mixture of 99 wt. % of a 50/50 PEGT/PBT copolymer, wherein the polyethylene glycol has a molecular weight of 300, and 1 wt. % of α-tocopherol;
 (ii) 2 wt. % of 1-ascorbic acid 6-palmitate;
 (iii) 4 wt. % of cholesterol; and
 (iv) 5 wt. % of enkephalin peptide.
Microsphere B
 (i) 85 wt. % of a mixture of 98.5 wt. % of a 70/30 PEGT/PBT copolymer, wherein the polyethylene glycol has a molecular weight of 2,000, and 1.5 wt. % of the antioxidant Trolox-NH-PEG 1,000-OCH$_3$
 (ii) 5 wt. % of polyethylene glycol having a molecular weight of 2,000; and
 (iii) 10 wt. % of insulin.

The synthesis of Trolox-NH-PEG 1,000-OCH$_3$ is described in Example 3 hereinbelow.
Microsphere Preparation via the Spray Drying Technique Preparation of the PLGA microspheres using the spray drying technique has been published in the literature (Gander, et al., *Microencapsulation*, Vol. 12, pgs. 83–97 (1995)). It was shown that PolyActive microspheres could also be prepared by the spray drying technique. In contrast to the solvent evaporation technique, only low concentrations of PEGT/PBT in CH$_2$Cl$_2$ (2%) could be used to prepare microspheres, because at higher concentrations PEGT/PBT fibers were formed. The characteristics of the PEGT/PBT and PLGA microspheres prepared via the spray drying technique are given in Table II.

TABLE II

Characteristics of Polyactive (PA)/PLGA microspheres prepared by the spray drying technique

| batch no. | polymer; concentration % (w/v) | Yield (%) | protein and encapsulation efficiency | Size (μm) number wght | Size (μm) volume wght |
|---|---|---|---|---|---|
| 34 | PLGA; 5% | 30 | BSA; 48% | 3 | 6 |
| 35 | PA 70/30; 2% | 53 | DT | 7 | 16 |
| 36 | PA 60/40; 2% | 40 | DT | 16 | 84 |
| 37 | PA 70/30; 2% | 58 | BSA | 11 | 83 |
| 38 | PA 70/30; 2% | 43 | IgG | 10 | 259 |
| 39 | PA 70/30; 2% | 42 | lysozyme | 17 | 136 |

The particle size distribution for PEGT/PBT microspheres prepared via the spray drying technique is substantially broader as compared with the spray dried PLGA microspheres. This is especially the case for the protein loaded PEGT/PBT microspheres.
Protein Encapsulation Efficiency The encapsulation efficiency of BSA could be determined by dissolving an aliquot of the microspheres in a suitable solvent (CH$_2$Cl$_2$) followed by extraction with water. Using this procedure BSA was extracted almost quantitatively. This procedure was validated by extracting a solution of PLGA in CH$_2$Cl$_2$ containing a known amount of BSA.

It appears that the encapsulation efficiency in PEGT/PBT microspheres was high (50–100%, Table I) and hardly dependent on the processing parameters. The concentration of protein in the PVA phase and the different washing solutions also was determined in order to establish the mass balance. Table III summarizes the results.

TABLE III

BSA encapsulation efficiency in PolyActive and PLGA microspheres

| Batch | Polymer | PVA | Wash I | Wash II | Wash III | ms* | recovery** (%) |
|---|---|---|---|---|---|---|---|
| 16 | PA 70/30; | 8.2 | 0.3 | 0 | 0 | 70.3 | 92 |
| 17 | PA 70/30; 10% | 2.0 | 0 | 0 | 0 | 76.5 | 92 |
| 18 | PA 70/30; 20% | 2.4 | 0.1 | 0 | 0 | 35.0 | 44 |
| 19 | PA 60/40; | 3.1 | 0 | 0 | 0 | 74.3 | 91 |
| 20 | PA 60/40; 10% | 2.8 | 0.1 | 0 | 0 | 21.8 | 29 |
| 21 | PLGA; 5% | 14.7 | 1.1 | 0.9 | 1.0 | 57.8 | 88 |
| 22 | PLGA; 10% | 0.4 | 0 | 0 | 0 | 55.7 | 65 |

*BSA content (mg) of the microspheres as determined by the extraction method
**BSA detected in the microspheres, PVA and washing solutions/BSA offered for encapsulation (=85 mg)

From this table it clear that the mass balance (% recovery) is good, except for 2 formulations. The low recovery for Batch 18 and Batch 20 can probably be ascribed to the low recovery of the microspheres (see Table I).

From the literature it is known that for encapsulation efficiency of proteins in PLGA (and other matrices) is highly dependent on the stability of the water-in-oil emulsion. Obviously, this is ensured by using the Ultraturrax as hereinabove described. The encapsulation efficiency of diphtheria toxoid therefore was determined from the diphtheria toxoid concentrations in the PVA external phase and the different washing solutions. It was shown that the amount of the diphtheria toxin in these solutions was less than 15% (encapsulation efficiency greater than 85%), except for the PEGT/PBT 70/30 (10%) and the PLGA (10%) microsphere batches.
Scanning Electron Microscopy Analysis SEM was used to evaluate the shape and surface characteristics (porosity) of the microspheres. The following trends were found:

Microspheres prepared using the solvent evaporation technique are perfectly spherical. This is especially true for microspheres which were prepared using a high concentration of PolyActive in CH$_2$Cl$_2$. Microspheres prepared using the spray drying technique did not have perfectly round shape as observed for the solvent evaporation particles. In the protein loaded microspheres pores sometimes can be observed. These pores might contribute to and be related to the sometimes observed burst release of the proteins.
Release of BSA from PA and PLGA Microspheres The release of BSA from PA and PLGA microspheres prepared by the solvent evaporation technique and from the one batch (PLGA) prepared by the spray drying technique was evaluated. The release of BSA from the microspheres of PA 60/40, PA 70/30 and PLGA over a period of 150 days in given in FIGS. 4, 5, and 6. The results are summarized in Table IV below.

TABLE IV

Release of BSA from PA and PLGA microspheres

| Microsphere | Particle Size (μm) Number | Particle Size (μm) Volume | BSA Loading (mg BSA/g ms) | burst* μg/g; % | release** μg/g; day |
|---|---|---|---|---|---|
| PA 70/30; 5% | 14 | 57 | 66.9 | 158; 2.3 | 21.3 |
| PA 70/30; 10% | 9 | 65 | 37.4 | 2.2; 0.1 | 8.7 |
| PA 70/30; 20% | 19 | 369 | 12.1 | 40; 3.5 | 21.3 |
| PA 60/40; 5% | 11 | 43 | 60.5 | 240; 3.8 | 4.9 |
| PA 60/40; 10% | 17 | 444 | 17.8 | 177; 9.1 | 4.9 |
| PLGA; 5% | 8 | 29 | 52.6 | 3500; 65 | 0 |
| PLGA; 10% | 9 | 65 | 27.1 | 100; 3.6 | 0 |
| PLGA; SD | 3 | 6 | 18500 | 18500; 100 | 0 |

*arbitrarily taken as the amount of protein released during the first 5 hours.
** calculated from the amount of protein released from day 1–150.

Figure 4:
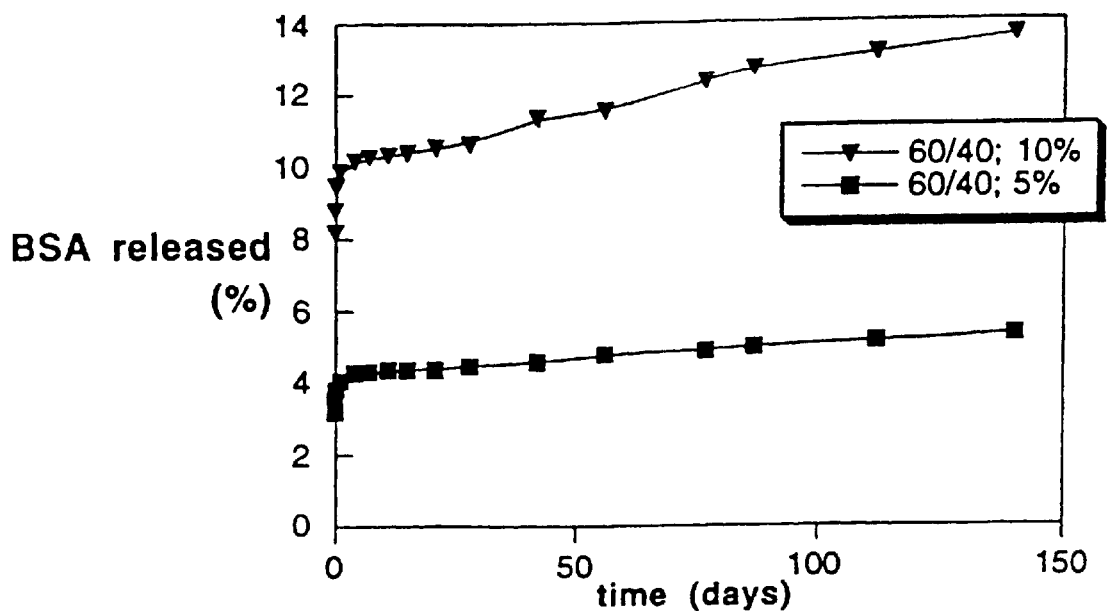
FIG. 4 is a graph showing the release of bovine serum albumin (BSA) from PolyActive (PA) 6/40 microspheres over a period of 150 days.
Figure 5:
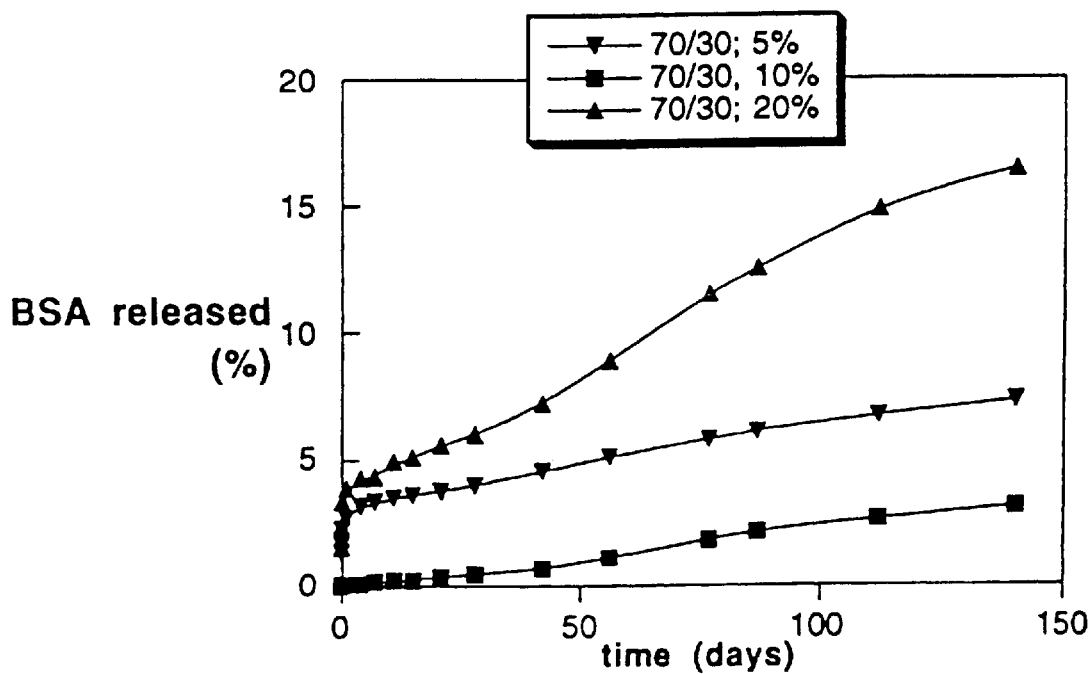
FIG. 5 is a graph showing a release of BSA from PA 70/30 microspheres over a period of 150 days.
Figure 6:
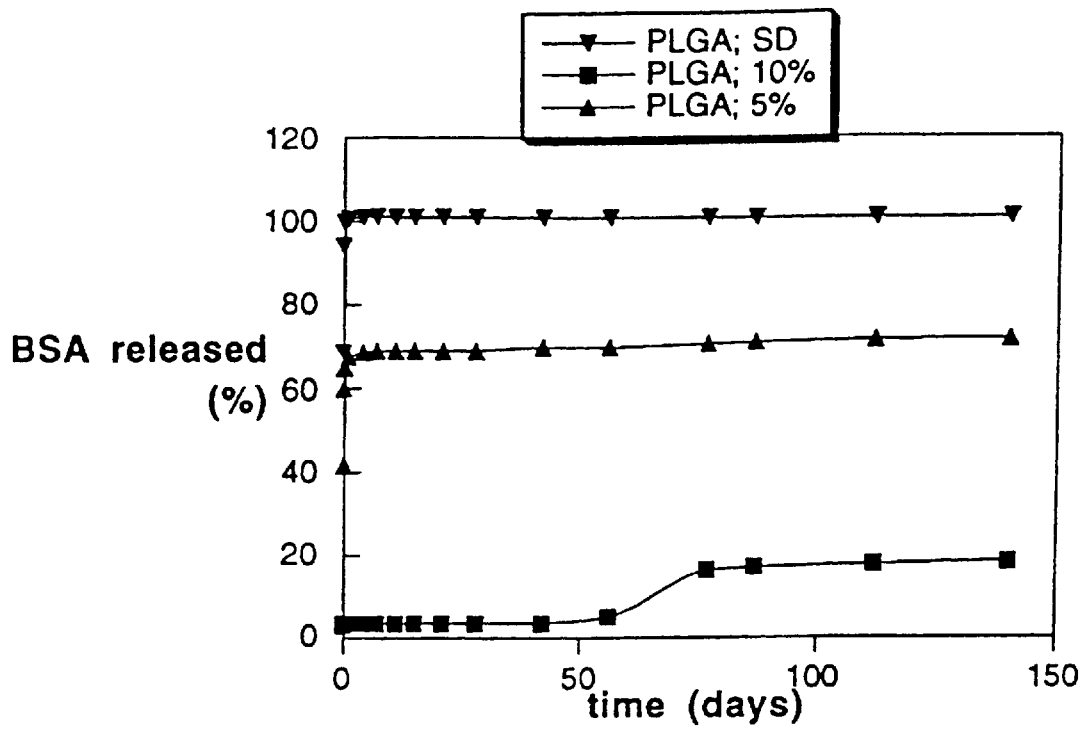
FIG. 6 is a graph showing the release of BSA from PLGA microspheres over a period of 150 days.

From FIGS. 4, 5, and 6 and Table IV, it appears that the release of BSA from PEGT/PBT microspheres is associated with a very small burst effect (maximum 10%). After the burst release, a sustained release of BSA is observed. The slow (sustained) release of BSA from the PEGT/PBT 70/30 and 60/40 microspheres is probably due to the diffusion of BSA through the (homogenous) matrix. Moreover, this release was more pronounced for the more hydrophilic microspheres. (PEGT/PBT 70/30; 9–21 μg BSA/g ms.day) as compared with the more hydrophobic 60/40 microspheres (5 μg BSA/g ms.day), indicating the diffusivity of BSA is greater in the PEGT/PBT 70/30 matrix than in the 60/40 matrix. This can be attributed to the higher equilibrium water content of the PEGT/PBT 70/30 microspheres as compared with the PEGT/PBT 60/40 microspheres. It also is noted that during the release time (150 days) probably no substantial degradation of the matrix occurs. Again, in oxidative environments the degradation is faster than in PBS, which might have a pronounced effect on the in vivo release of the BSA from PEGT/PBT microspheres.

In contrast to the PEGT/PBT microspheres, 2 out of 3 PLGA microsphere preparations showed a pronounced burst release (FIG. 6). Especially the spray dried (abbreviated: SD) microspheres and the microspheres prepared using a low PLGA concentration (5%) showed this high outburst release, which can be ascribed to the porous character of the particles. On the other hand, the PLGA microspheres prepared using high PLGA concentration showed a marginal burst release. In addition, this batch showed a pulsed release of encapsulated BSA between 60 and 80 days. The pulse corresponds with the degradation (dissolution) time of these microspheres. However, it is remarkable that the percentage of BSA release did not reach 100%. Part of the protein may be denatured (precipitated) due to the low pH generated in the degrading microspheres.

Release of Diphtheria Toxoid from PA and PLGA Microspheres

Figure 7:
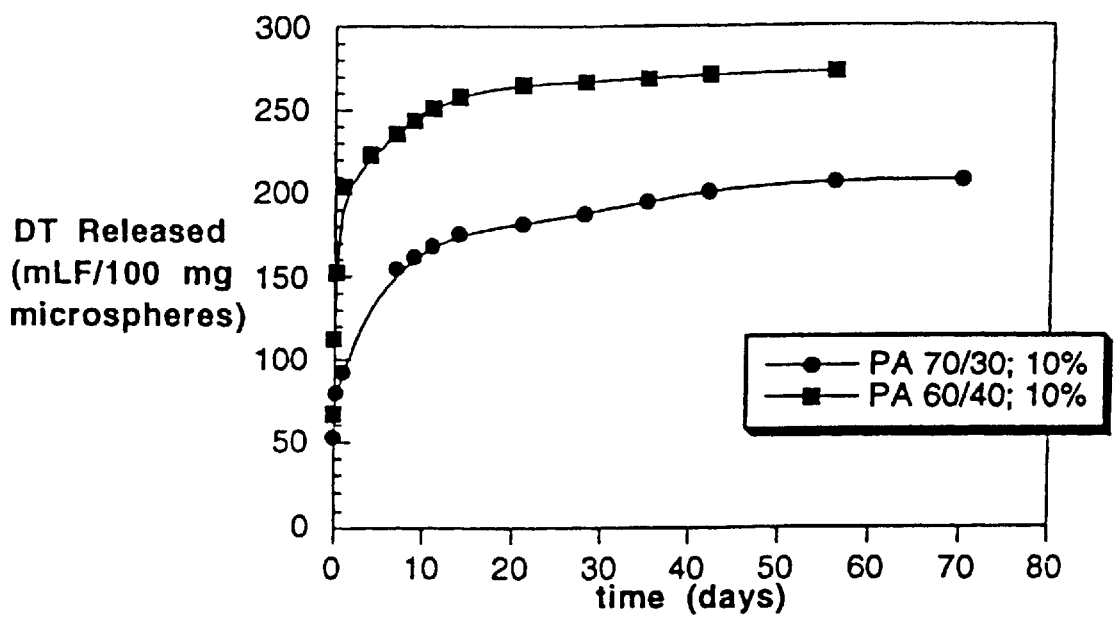
FIG. 7 is a graph showing the release of diphtheria toxoid from PEGT/PBT 70/30 and 60/40 microspheres.

FIG. 7 shows a representative example of the release of diphtheria toxoid from PEGT/PBT 70/30 and 60/40 microspheres. The release was followed for a period of up to 10 weeks. In general, a burst release was observed followed by a continuous release from day 1 to day 20, after which a very low release of diphtheria toxoid was observed for the next 50 days. Table V summarizes the results.

TABLE V

Release of diphtheria toxoid from PEGT/PBT microspheres

| microsphere | particle size (μm) number | particle size (μm) volume | Release (LF/g) burst* | Release (LF/g) day 1–21 | Release (LF/g) day 21–70 |
|---|---|---|---|---|---|
| PEGT/PBT 70/30; 5% | 5 | 21 | 7.5 | 1.4 | .24 |
| PEGT/PBT 70/30; 10% | 9 | 70 | .9 | .9 | .26 |
| PEGT/PBT 70/30; 20% | 12 | 202 | 1.6 | .22 | .09 |
| PEGT/PBT 70/30; 20% | 9 | 145 | .5 | .15 | .03 |
| PEGT/PBT 70/30; SD | 7 | 16 | 123 | 1.9 | .46 |
| PEGT/PBT 60/40; 5% | 6 | 28 | 1.3 | .25 | .11 |
| PEGT/PBT 60/40; 10% | 13 | 51 | 1.8 | .55 | .07 |
| PEGT/PBT 60/40; SD | 16 | 84 | 88 | 5.1 | 3.0 |
| PLGA; 5% | 7 | 16 | 24 | 2.4 | .61 |
| PLGA; 10% | 8 | 41 | 2.0 | .15 | .043 |

*arbitrarily taken as the amount of protein released during the first day.

Taken into account that around 200 LF diphtheria toxoid per gram microsphere was encapsulated, it appears that the burst release of diphtheria toxoid from PEGT/PBT microspheres prepared by the solvent evaporation technique is relatively low. After the burst release, the PEGT/PBT particles showed a gradual release up to 70 days after the start of the release experiment.

In contrast to microspheres prepared by the solvent evaporation technique, the particles prepared by spray drying technique showed a very significant burst release (around 50%) which can probably be ascribed to the porous character of particles prepared via this technique. Like the "solvent evaporation" particles, the spray dried particles showed a gradual release after the burst release. The release rate (from day 1–21 and 21–70) of diphtheria toxoid was higher from the spray dried particles than for the "solvent evaporation" particles. Obviously, the release (after the burst) from the "solvent evaporation" particles is determined by the diffusion of diphtheria toxoid through the homogeneous polymer matrix, whereas the release from the "spray dried" particles is also determined by the diffusion of the protein through the pores present in the matrix. In contrast to PLGA microspheres which contained BSA (FIG. 6), for the PLGA microspheres containing diphtheria toxoid, no pulsed release is observed between day 60 to 80 (dissolution time of the PLGA microspheres). This may be caused by the low stability of diphtheria toxoid at the low pH generated in the degrading matrix.

Figures 8, 9:
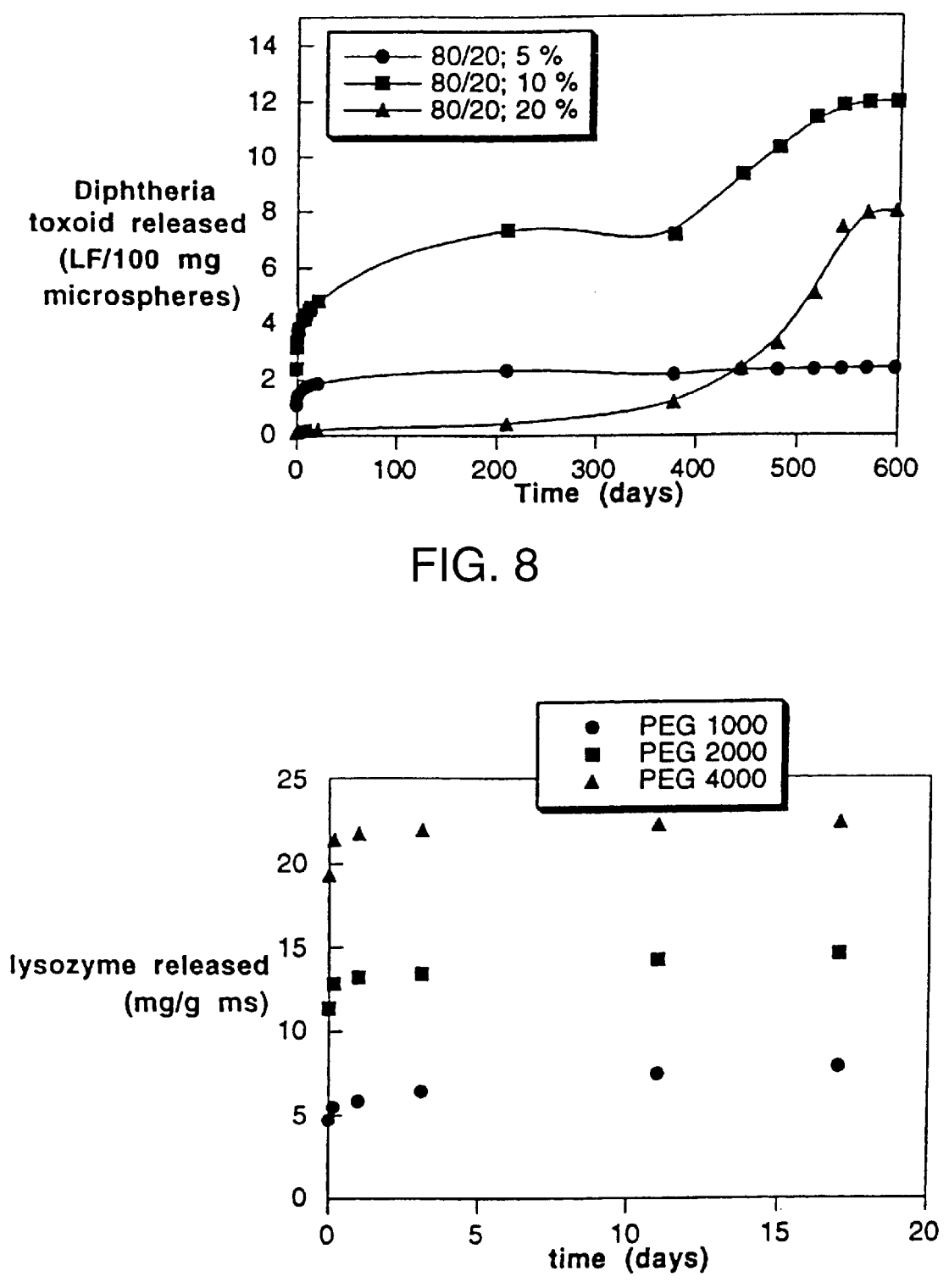

The release of diphtheria toxoid from PEGT/PBT (80/20) microspheres (prepared by solvent evaporation technique) was followed for a period of almost 600 days (FIG. 8).

The microspheres prepared from a 5% PEGT/PBT 80/20 solution in $CH_2Cl_2$ showed a substantial burst release of around 50–60% of the encapsulated diphtheria toxoid. Thereafter, a gradual release of the protein occurred within the following 20 days. The 10% PEGT/PBT microspheres showed a (smaller) burst release of around 10–20% of the encapsulated amount of protein, followed by a gradual release up to 200 days and by an additional release starting around 400 days and ending after 550 days. The 20% PEGT/PBT 80/20 microspheres showed a marginal burst release (1–2%), followed by a gradual release up to 400 days after which the remaining encapsulated diphtheria toxoid is released in a pulse. For the 5% PEGT/PBT 80/20 microspheres no pulse after 400 days was observed. This can be ascribed to the rather porous character of the microspheres and/or to the low encapsulation efficiency of diphtheria toxoid in these particles.

The observed release profiles can be explained as follows. The burst release is due to protein present at or near the surface of the microspheres and the protein present in pores. An increasing concentration of PEGT/PBT (5–20%) resulted in microspheres with a less porous character and consequently a reduced in a reduced burst release. The gradual release followed after the burst release is due to diffusion of the protein through the (non-porous) matrix. The release starting around 400 days can be ascribed to degradation of the matrix. The degradation was associated with increased swelling of the microspheres (visual observation).

The observed release profile of diphtheria toxoid from PA 80/20 microspheres is very interesting for the design of new vaccine formulations. It can be envisaged that by mixing diphtheria toxoid containing microspheres with a varying degradation (dissolution) time, diphtheria toxoid (antigens in general) can be released in multiple pulses which is considered necessary for obtaining a protective immune response.

When it is assumed that after 600 days all encapsulated diphtheria toxoid has been released, an estimation can be made on the DT encapsulation efficiency (Table VI)

TABLE VI

Encapsulation efficiency of diphtheria toxoid in PolyActive microspheres

| Batch | DT (in LF) released in 600 days | sample size (mg) | yield (mg) | DT encapsulated LF; %* |
|---|---|---|---|---|
| PA 80/20; | 2.4 | 102 | 740 | 17; 2% |
| PA 80/20; 10% | 11.9 | 104 | 1700 | 195; 24% |
| PA 80/20; 20% | 8.0 | 107 | 3200 | 239; 30% |

*810 LF were offered for encapsulation

Agian it appears that the encapulation efficiency is low when a diluted solution of PA (5%, w/v) is used for the encapulation process.

Release of Lysozyme from PEGT/PBT Microspheres

The effect of the molecular weight of the PEG block of PolyActive was evaluated by studying the release of protein with a relatively low molecular weight (lysozyme, M-14.3 kD) from PA 80/20 microspheres with a varying PEG molecular weight (1,000, 2,000, and 4,000 g/mol). It is expected that a molecule of a higher weight of the PEG block will result in larger hydrophilic PEG domains in the PEGT/PBT matrix, which will facilitate the diffusion of the encapsulated protein. The initial release (up to 17 days) has been measured. FIG. 9 shows the release of lysozyme from PA 80/20 microspheres.

Figure 10A:
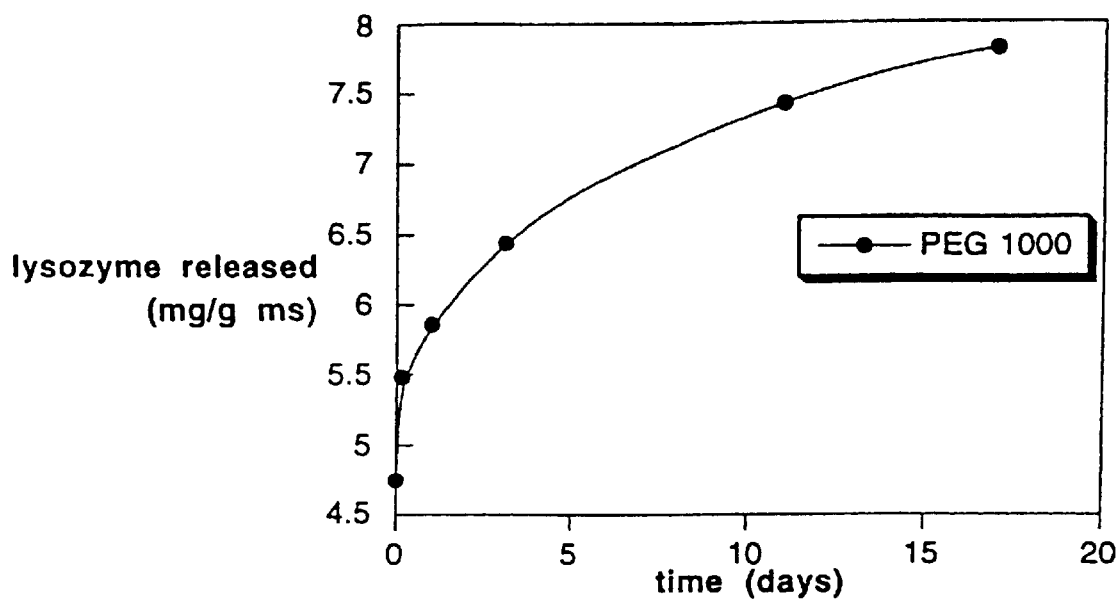
FIG. 10A is a graph showing the release of lysozyme from PEGT/PBT 80/20 microsheres as a function of time.

A burst release of lysozyme from PEGT/PBT microspheres is observed followed by a more gradual release. Because the encapsulated amount of protein in the different microspheres is not known, the observed burst release cannot be expressed in % of the core loading. When it is assumed that the encapsulation efficiency was 100%, the burst release is about 10, 20, and 40% for the PEGT/PBT 80/20 (1000), PEGT/PBT 80/20 (2000), and PEGT/PBT 80/20 (4000), respectively. The real burst release will be greater because the encapsulation efficiency will be less than assumed. This means that lysozyme shows a pronounced burst release from the 80/20 microspheres. This is probably caused by the low concentration of PEGT/PBT used (5%) for the preparation of the particles which provides a porous structure. After the burst release, all PEGT/PBT 80/20 particles showed a gradual release. This is shown in detail for one microsphere preparation in FIGS. 10A (release versus time) and 10B (release versus square root of time).

Figure 10B:
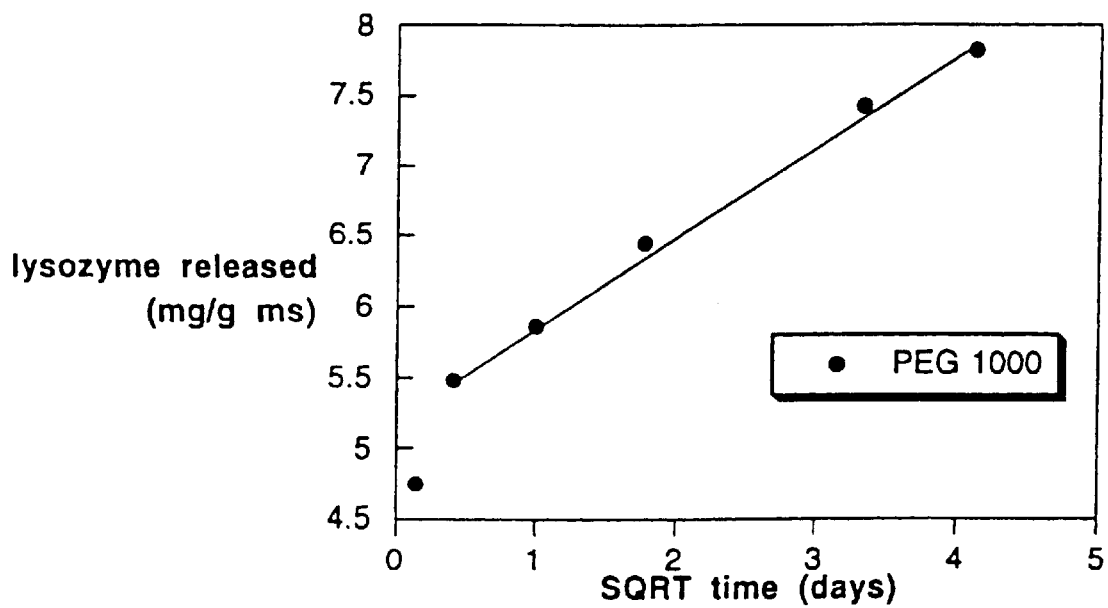
FIG. 10B is a graph showing the release of lysozyme from PEGT/PBT 80/20 microspheres as a function of the square root of time.

FIG. 10B shows that the cumulative release (after the burst release) was proportional to the square root of time, which is indicative for a diffusion controlled release. The other microsphere also showed a square root of time dependency of the release (results not shown).

Aging of PA and PLGA Microspheres

Figure 11:
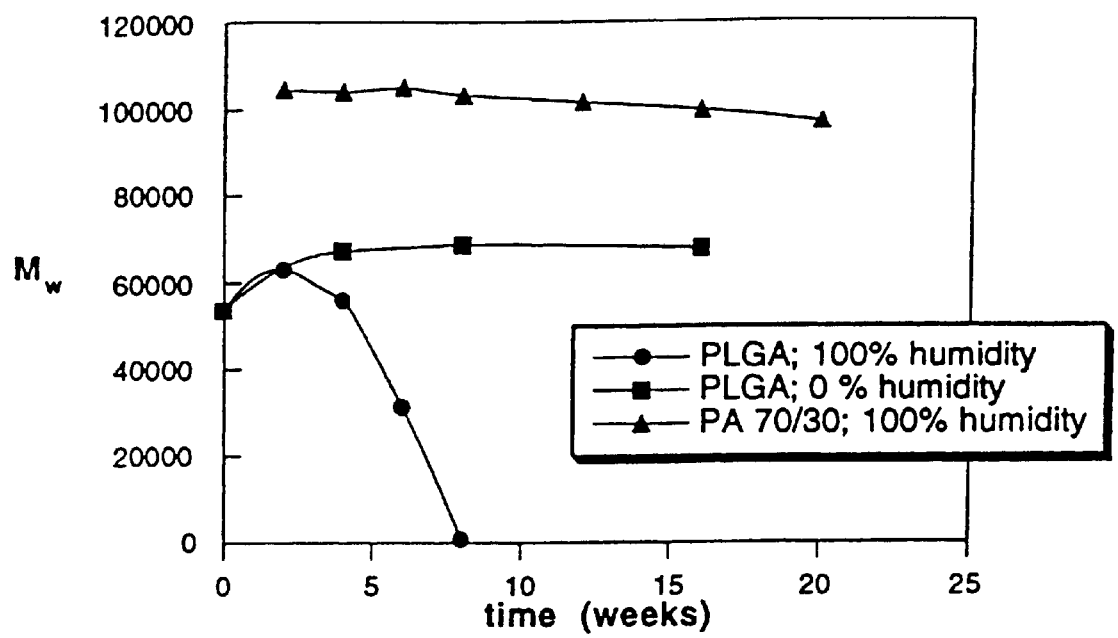
FIG. 11 is a graph showing the molecular weight of PolyActive and PLGA as a function of the incubation time.

PEGT/PBT and PLGA microspheres were aged at 37° C. and at 100 and 0% relative humidity, respectively. Aging was followed by measuring the molecular weight of the polymer. FIG. 11 shows the molecular weight of PA and PLGA as a function of the incubation (aging) time.

It appears that PLGA is degraded rapidly in a humid atmosphere. Within 8 weeks the particles were completely degraded. This is even faster than the degradation time of the same particles in a buffer solution of pH 7.2. (degradation time 10–12 weeks). The fast degradation of PLGA at 100% humidity can be explained as follows. Initially, the (dry) PLGA microspheres absorb some water. This results in hydrolysis of ester bonds, yielding carboxylic acid residues. These acidic groups catalyze a further hydrolysis of the polyester backbone, finally resulting in water soluble oligomers and monomers. In buffered solutions part of the formed acid residues are neutralized and/or diffused out of the microparticles resulting in a retarded degradation as compared with particles aged in a humid environment. On the other hand, both microspheres of PEGT/PBT 60/40 and PEGT/PBT 70/30 were stable at 100% humidity (no significant change in molecular weight over a period of 20 weeks). FIG. 11 shows the results for PEGT/PBT 70/30. Comparable results were obtained for PEGT/PBT 60/40. This again demonstrates that PEGT/PBT degrades more slowly than PLGA in a humid environment. Further, it was shown that PEGT/PBT microspheres (Batch 12 70/30) absorbed water under the aging conditions. The equilibrium water content (Karl Fischer titration performed by Dr. J. Goedemoed) amounted to 16 and 25% (w/w) after 1 and 2 weeks aging respectively. Obviously the water present in the microspheres did not cause any significant hydrolysis (degradation) of the polymer. In a non-humid environment, both PLGA and PA were stable: no drop in molecular weight was observed.

EXAMPLE 2

Six polyethylene glycol terephthalate/polybutylene terephthalate (PEGT/PBT) copolymers were synthesized. In three of the copolymers, the polyethylene glycol had a molecular weight of 1,000. (PEG 1,000). These three copolymers had weight percentage ratios of PEGT/PBT of 40/60, 60/40, and 80/20. In the other three copolymers, the polyethylene glycol had a molecular weight of 600. (PEG 600). These three copolymers had weight percentage ratios of PEGT/PBT of 40/60, 60/40, and 77/23. Each of the six copolymers contains 0.4 wt. % of the antioxidant 1,3,5-trimethyl-2,4,6-tris(3,5-di-tert-butyl-4-hydroxybenzyl) benzene sold by Ciba-Geigy as Irganox 1330.

Disks were then made of each copolymer. Each disk included indomethacin in an amount of 5 wt. %. Indomethacin is 1-(p-chlorobenzoyl)-5-methoxy-2-methyl-3-indole-3-acetic acid, has a molecular weight of 357.8, and has the following structure:

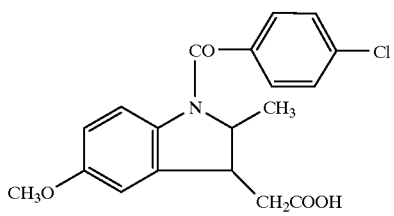

Disks which included PEGT/PBT copolymer wherein the PEGT/PBT weight ratio was 40/60, and the molecular weight of polyethylene glycol in the polymer was 1,000, were made by forming a solution of 6.34 g PEGT/PBT, 73.36 g of chloroform, and 5 g of hexafluoroisopropanol. (HFIP). This solution then was mixed with a solution of 0.333 g of indomethacin, 10 g of chloroform, and 50 μl HFIP in a Petri dish having a diameter of 9 cm. Prior to mixing, the polymer was allowed to dissolve overnight. A small amount of HFIP increases the dissolving rate of the drug considerably. Disks having a diameter of 5 mm then were made by punching the resulting film formed by the combination of the solution with a cork borer. Also, disks were made from small quantities of polymer/drug solution which was not poured into the Petri dish.

For the polymers in which the polyethylene glycol has a molecular weight of 1,000 and which have a PEGT/PBT weight ratio of 60/40 and 80/20, and for the polymers having a polyethylene glycol molecular weight of 600, a solution of 3.5 g of polymer and 35 g of chloroform, and a solution of 0.184 g of indomethacin, 5.53 g of chloroform, and 50 μl of HFIP were combined in a Petri dish having a diameter of 5 cm.

The PEG 600 40/60 copolymer showed an extensive shrink; the resulting layer possessed a thickness such that one 5 mm disk had a weight of 90–99 mg. For all other polymers, it was necessary to combine 3 to 5 disk layers.

Flow-Through Elution

Release studies were performed by use of flow cells. The flow cells were filled with tiny glass beads. 9 cells possessed an internal diameter of 22.6 mm and 9 other cells 12.0 mm. Because of the very low flow rate (1 ml/hr), it is very likely that cell dimension is not very critical in the release process.

The 18 flow cells were supplied with eluant with 2 Harvard Infusion syringe pumps (type Pump 22, microprocessor controlled). Each pump has been modified in such a way that 9 syringes of 100 ml can be placed on a holder. The extended plungers of the syringes were pushed continually in a horizontal direction by a moving bar.

Eluant composition: phosphate buffer 0.05 M, pH 7.4, isotonic

| | |
|---|---|
| NaH$_2$PO$_4$.1H$_2$O | 3.65 g |
| Na$_2$HPO$_4$ (Anhydrous) | 5.7 g |
| NaCl | 9.2 g |
| NaN3 | 0.5 g |
| purified water | 2.0 l |

Samples were taken after 2, 4, 8 and 14 hours, and after 1, 2, 3, 7.25 and 8.25 days. During 30 min an Eppendorf cup was filled with 0.5 ml. Hereafter the cups were closed and frozen in liquid nitrogen.

Analysis of Indomethacin

The liquid chromatographic system consisted of a Pharmacia analytical pump (Type 2248) with solvent conditioner, a Pharmacia variable wavelength monitor, a Pharmacia high sensitivity flow cell, a Marathon autosampler with 20 μl sample loop and a Pharmacia HPLC computing system with a Tandon 1 MB Ram computer with Star LC-20 printer.

A Zorbax RP8 Stable Bond (Rockland Technologies) column (150×4.6 mm) packed with 5 μm spherical particles was used. The wavelength was set at 254 nm. The mobile phase consisted of acetonitrile/1.3% v/v acetic acid in water 65/35. The flow rate was 1.0 ml/min. All separations were affected isocratically at ambient temperature.

Standards of indomethacin have been prepared, using the same flow through eluant, of 100, 50, 20, 10, 5, 2 and 1 μg/ml. Shortly after preparation the standards have been dispensed in 1.5 ml polypropylene Eppendorf cups and frozen in liquid nitrogen, in order to limit degradation phenomena prior to analysis. Samples from the flow-through system have been injected directly in the chromatographic system after melting.

Assay of Indomethacin in PEGT/PBT Disks

The dried disks were cut into tiny pieces, accurately weighed and dissolved in chloroform (40/60 in 50 ml, 60/40 and 80/20 in 25 ml) overnight. Standards have been prepared by dissolving indomethacin in chloroform and appropriately diluting to 50, 20, 10, 5 and 2 μg/ml.

Results

Preparation of Devices

The indomethacin containing PEGT/PBT devices were yellow colored and had an opaque appearance. The evaporation process occurred over a period of 3 to 5 days. This slow rate was necessary for obtaining films with regular thickness. After 8.25 days elution, the cylindrical shape of all 18 devices were the original disk-layers separated.

After 8.25 days elution and evaporating/drying at 85° C., the 40/60 devices showed a tough constituence, the 60/40 devices a moderate, and the 80/20 devices a relatively soft constituence.

Water Uptake Data

Water uptake data for the disks with respect to flow-through elution at 8.25 days are given in Table VII. As a control, water uptake data for injection molded cylinders also are provided.

TABLE VII

Water uptake of Polyactive devices after 8.25 days flow-through elution

| Polymer | weight* before start (mg) | % water uptake* after 8.25 days (w/w) | % water uptake** injection molded cylinder (w/w) |
|---|---|---|---|
| PEG 1000 40/60 | 107 | 7 | 15 (1 wk) |
| PEG 1000 60/40 | 113 | 43 | 37 (1 wk) |
| PEG 1000 8o/20 | 97 | 78 | 75 (24 hrs) |
| PEG 600 40/60 | 93 | 14 | 18 (24 hrs) |
| PEG 600 60/40 | 102 | 21 | 25 (24 hrs) |
| PEG 600 77/23 | 129 | 23 | 42 (24 hrs) |

*average of 3 cylindrical devices containing 5% indomethacin
**cylinders d = 10 × 20 mm For PEG 600 77/23, considerably less water-uptake has been observed, possibly due to the extra hydrophobic influence of 5% w/w indomethacin. Also, the other two PEG 600 formulations had somewhat lower uptake percentages. In the PEG 1000 series, the 40/60 polymer showed a water uptake of half of that of the injection molded reference.

Flow-Through Release Results

Figure 12:
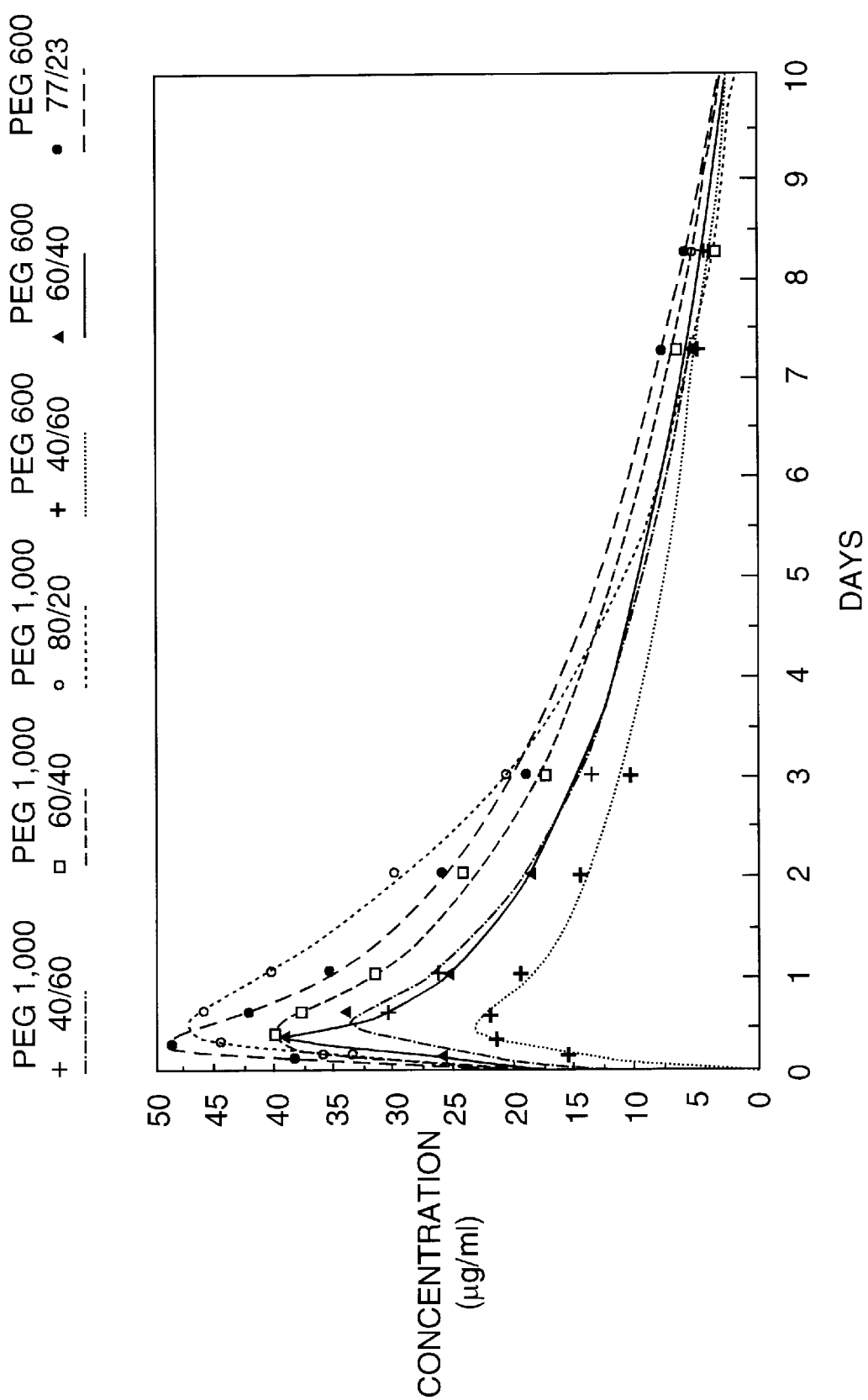
FIG. 12 is a graph showing indomethacin release profiles from disks made from 6 PEGT/PBT polymers.

Indomethacin release profiles from disks made from each of the 6 PEGT/PBT polymers are shown in FIG. 12. The ratio between the most rapid and the slowest indomethacin release is less than 2. After 8.25 days, 3.68 mg of indomethacin was released from the disks formed from the PEG 1000 80/20 polymer, and 2.05 mg of indomethacin was released from the disks formed from the 600 40/60 polymers.

Indomethacin Analysis

With the applied chromatographic method, indomethacin showed a retention time of 3.3 min., with no interfering peaks in its proximity. After 8.25 days elution, a peak at 2.6 min slightly and a complex of peaks around 2 min. increases considerably. The chromatogram of an indomethacin standard in phosphate buffer (2 μg/ml) shows that at least one peak of the complex originates from indomethacin itself.

In the chromatogram resulting from the indomethacin assay of the PolyActive device remnants, an extra peak at a retention time of 2.8 min can be seen, which reflects the antioxidant Irganox 1330 or one or several oxidized forms of this compound.

The above analyses of indomethacin have been taken into consideration when determining the weight loss of polymer after 8.25 days elution. Weight losses for disks formed from each of the six polymers are given in Table VIII below.

TABLE VIII

| | weight before start (mg) | weight w/out indomethacin | weight after drying | % polymer weight loss |
|---|---|---|---|---|
| PEG 1000 40/60 | 107 | 102 | 80 | 22 |
| PEG 1000 60/40 | 113 | 108 | 105 | 3 |
| PEG 1000 80/20 | 97 | 92 | 87 | 5 |
| PEG 600 40/60 | 93 | 90 | 85 | 6 |
| PEG 600 60/40 | 102 | 98 | 93 | 5 |
| PEG 600 77/23 | 129 | 123 | 107 | 13 |

Preparation of Indomethacin-Containing Microspheres

Also prepared by the solvent evaporation technique hereinabove described in Example 1 were the following microspheres containing indomethacin.

Microsphere C
(i) 89 wt. % of a mixture of 99 wt. % of a 50/50 PEGT/PBT copolymer, wherein the polyethylene glycol has a molecular weight of 300, and 1 wt. % of α-tocopherol;
(ii) 1 wt. % of 1-ascorbic acid 6-palmitate;
(iii) 5 wt. % of cholic acid; and
(iv) 5 wt. % of indomethacin.

Microsphere D
(i) 94 wt. % of a mixture of 99 wt. %; of a 50/50 PEGT/PBT copolymer, wherein the polyethylene glycol has a molecular weight of 300, and 1 wt. % α-tocopherol;
(ii) 1 wt. % 1-ascorbic acid 6-palmitate; and
(iii) 5 wt. % indomethacin.

Microsphere E
(i) 95 wt. % of a mixture of 99.5 wt. % of a 50/50 PEGT/PBT copolymer, wherein the polyethylene glycol has a molecular weight of 300, and 0.5 wt. % α-tocopherol; and
(ii) 5 wt. % indomethacin.

Microsphere F
Same as Microsphere E, except that the polyethylene glycol of the PEGT/PBT copolymer has a molecular weight of 400.

Microsphere G
Same as Microsphere E, except that the PEGT/PBT ratio of the PEGT/PBT copolymer is 55/45.

EXAMPLE 3

The polymeric materials used in this example were (i) a PEGT/PBT copolymer having a PEGT/PBT ratio of 70/30 and wherein the polyethylene glycol had a molecular weight of 1,000, and wherein such material included 0.5 wt. % of the antioxidant d,1 α-tocopherol; and (ii) a PEGT/PBT copolymer having a PEGT/PBT ratio of 70/30, and a polyethylene glycol molecular weight of 1,000, wherein such material also included the antioxidant Trolox-NH-PEG 1,000 —OCH$_3$. The Trolox-derived antioxidant was synthesized by dissolving 5.00 g of Trolox, which has the following structure:

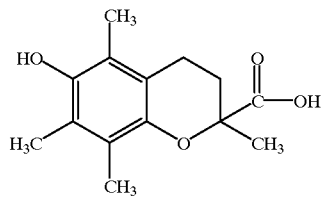

in a mixture of 100 ml dioxane and 100 ml dichloromethane and 5 ml (1.5 eq) triethylamine at room temperature. The clear solution was cooled to −15° C., and 2.01 ml (19.5 mmole) of ethyl chloroformate in 20 ml dichloromethane was added dropwise and the resulting suspension was stirred for 10 minutes at −15° C. A solution of 10.0 g (10 mmole) of $(CH_2—CH_2—O)_{21}—NH_2$ in 60 ml dioxane (with 1 ml triethylamine) was added and the cooling bath was removed. The reaction mixture was allowed to warm to room temperature in about 1 hour. The solvent was removed in vacuo and the residue was dissolved in 100 ml of 1 M HCl solution and extracted twice with 50 ml of ethyl acetate. The aqueous layer was neutralized to pH 12 with solid $K_2CO_3$ and extracted three times with 50 ml of ethyl acetate. (The product forms an intermediate layer. This layer was combined with the ethyl acetate layer.) 50 ml of 2-propanol then was added to the combined organic layers, and the layers then were dried with $Na_2SO_4$ and concentrated in vacuo to give 10.61 g (86%) of crude product.

The crude product was purified by chromatography (Silicagel 60, with methanol as eluant). The ninhydrin-negative fractions with an Rf value of 0.3–0.1 were combined and concentrated in vacuo to give an almost colorless oil (8.5 g, 69% yield), which solidified on standing. Several batches of the Trolox-PEG 1,000 derivative were prepared. In this example, 14.5 g of the Trolox-PEG 1,000 derivative are employed, whereby the Trolox-PEG 1,000 derivative is present in the matrix in an amount of 1.45 wt. %.

The particles of each polymer were melt fused to form porous cylindrical rods having a diameter of 12 mm and a length of 60 mm.

For both types of porous rods, 12×60 mm, partially gamma-irradiated in its usual packaging, disks of approximately 0.4 g were prepared using a cutting device. The preparations then were weighed and placed in 20.0 ml of testing medium.

Testing media employed in this example were as follows:
1. Nanopure water (having an electrical conductivity below 1 nano-Siemens per cm)
2. Physiological saline (0.9% NaCl)
3. Phosphate buffer 20 mM, pH 7.4
4. Phosphate buffer 50 mM, pH 7.4
5. Phosphate buffer 0.5 M, pH 7.4
6. Physiological saline with $H_2O_2$ (1 mM)
7. Nanopure water with Fe (100 $\mu$M)/$H_2O_2$ (1 mM) to generate hydroxyl radicals
8. Physiological saline with Fe (100 $\mu$M)/$H_2O_2$ (1 mM) to generate hydroxyl radicals.
9. Phosphate buffer, 20 mM, with Fe (100 $\mu$M), EDTA 100 $\mu$M/$H_2O_2$ (1 mM) to generate hydroxyl radicals, pH 7.4

In order to examine the influence of gamma-radiation on the non-irradiated PEGT 1,000/PBT 70/30 rods, the rods were incubated in the following media:
10. Physiological saline (0.9% NaCl)
11. Physiological saline with Fe (100 $\mu$M)/$H_2O_2$ (1 mM) to generate hydroxyl radicals.

Also, gamma-irradiated and non-irradiated including the Trolox antioxidant were incubated in the following media:
12. Gamma-radiation and physiological saline (0.9% NaCl)
13. Gamma-radiation and physiological saline (0.9% NaCl) with Fe (100 $\mu$M)/$H_2O_2$ (1 mM)
14. No radiation, physiological saline (0.9% NaCl)
15. No radiation, physiological saline (0.9% NaCl) with Fe (100 $\mu$M)/$H_2O_2$ (1 mM)

During the testing of these polymers, the following conditions also were employed.

Mass/Volume Ratio

1:50. A polymer sample of 400 mg was added to the liquid phase of 20 ml.

Bottle 40 ml cylindrical flasks, closed with plastic screw caps, were used (chemical grade glassware).

Temperature

The incubation temperature was 37° C.±0.5° C.

Pressure

Atmospheric Pressure.

Testing Periods

Polymer samples were tested at 0, 1, 2, 4, 8, 12, 26, 39 and 52 weeks.

Medium Change

All test media were changed once a week.

Agitation

No agitation.

Handling Prior to Testing

No drying procedure to constant weight of the test specimens was performed in order to prevent antioxidant content alterations.

Handling After Testing

At the end of the test period the device remnants were dried in an oven at 45° C. for 3 hours and weighed. It was expected that with decreasing PEGT-content of partially degraded devices the water content is a minor issue (<<1% w/w) after 3 hours drying at 45° C. Special care was taken during the change of the media at the stage of device fragmentation (approximately when $M_w$ has reached values below 40,000).

All test period resulting solutions were stored in the freezer below 0° C.

Number Tests

All tests were performed in triplicate.

A summary of media and number of specimens tested in each medium is given in Table IX below.

TABLE IX

| | 70/30 rod gamma-irradiated | | 70/30 rod non-irradiated | |
|---|---|---|---|---|
| medium no. | medium no. | test spec. no. | medium no. | test spec. no. |
| water | 1. | 24 | | |
| 0.9% NaCl | 2. | 24 | 10. | 24 |
| 20 mM phosphate | 3. | 24 | | |
| 50 mM phosphate | 4. | 24 | | |
| 0.5 M phosphate | 5. | 24 | | |
| 0.900 NaCl/1 mM H2O2 | 6. | 24 | | |
| 100 $\mu$M Fe/1 mM H2O2 | 7. | 24 | | |
| 0.9% NaCl/100 $\mu$M Fe/1 mM H2O2 | 8. | 24 | 11 | 24 |
| 20 mM phosphate/100 $\mu$M Fe/1 mM H2O2/100 $\mu$M EDTA | 9. | 24 | | |
| total no. test spec./bottles | | 216 | | 48 |

| | 70/30 rod gamma-irradiated Trolox-der. (sec. batch) | | 70/30 rod non-irradiated Trolox-der. (sec. batch) | |
|---|---|---|---|---|
| medium no. | medium no. | test spec. no. | medium no. | test spec. no. |
| 0.9% NaCl | 12. | 24 | 14. | 24 |
| 0.9% NaCl/100 $\mu$M Fe/1 $\mu$M H2O2 | 13. | 24 | 15. | 24 |
| total no. test specimens/bottles | | 48 | | 48 |

The following analyses were conducted on each of the polymer samples.

The intact devices were weighed after the drying procedure hereinabove described. When a device became fragmented, the tarrated glass bottle, after careful removal of the testing medium, was weighed as a whole after the same drying process.

pH measurements were performed in one of the triplicate test media just after the weekly medium change (accuracy within 0.01 pH unit).

GPC analysis was performed on all samples. Calibration was conducted with 12 standards ranging from 580 Daltons to 2,000,000 Daltons.

HPLC analysis of a $\alpha$-tocopherol was performed until no more $\alpha$-tocopherol could be measured from device remnants. The method was conducted by refluxing the device remnants with methanol, followed by HPLC reverse phase analysis using a Zorbax SB C8 column and 100% acetonitrile as an eluant.

HPLC analysis of aqueous solutions of terephthalic acid and its derivatives was conducted by HPLC reverse phase analysis using a Zorbax SB CN column with 30% acetonitrile/70% diluted acetic acid, 1.3% in water as the eluant.

UV spectrophotometric analyses for formic acid and acetic acid were conducted by applying enzymatic test combinations (formic acid: Boehringer Mannheim No. 979732; acetic acid: Boehringer Mannheim No. 148261). Testing solutions which have been shown to be acidified based on measured pH values are selected.

Results

Analysis of Trolox Antioxidant

Chromatographic analyses determined the purity of the Trolox derivative and indicated that no coupling occurred via the phenolic hydroxy group. HPLC detected free Trolox and its derivative. A free Trolox content in the derivative was determined to be about 1.2%. HPLC analysis of free $H_2N$-PEG 1,000-$OCH_3$, the other starting material, employing pre-column derivitization with F-moc-Cl, showed a free $H_2N$-PEG 1,000-$OCH_3$ content of about 0.35 wt. %. GPC analysis showed a monodisperse peak.

The following data in Table X below are given for two PEGT/PBT 70/30 batches synthesized on a 1 kg scale. Each polymer also includes α-tocopherol or Trolox derived antioxidant. The batch including the α-tocopherol antioxidant gave a synthesis yield of 870 g, and the batch including the Trolox-derived antioxidant gave a synthesis yield of 835 g. Molecular weight data were obtained by GPC using polystyrenes as calibrants, and % PEGT was calculated using H-NMR data.

TABLE X

| | $M_w$ | $M_w/M_n$ | % PEGT |
|---|---|---|---|
| α-tocopherol yield: 870 g | 107,222 | 2.144 | 70.1% |
| Trolox-derivative yield: 835 g | 103,285 | 2.065 | 71.1% |

Mw — Weight average molecular weight
Mn — Number average molecular weight

Before testing, several processing steps were conducted, including chopping of the granulate, sieving, drying, melt fusing, packaging, and in some cases, gamma-radiation.

In Table XI below, molecular weight data are given which represent three stages for each batch: (i) after synthesis as granulate; (ii) as a non-irradiated porous rod; and (iii) as a gamma-radiated porous rod.

TABLE XI

| α-tocopherol batch | Trolox derivative batch |
|---|---|
| granulate-Mw = 107,222 | granulate-Mw = 103,285 |
| non-irradiated porous rod Mw = 107,127 | non-irradiated porous rod Mw = 104,162 |
| gamma-radiated porous rod Mw = 102,294 | gamma-radiated porous rcd Mw = 97,665 |

The presented data for both batches are comparable; it shows that with both antioxidants completely comparable copolymer materials, with respect to molecular weight and PEGT/PBT ratio, can be obtained. Also, the Trolox antioxidant effectively protects the developing copolymer material during the polycondensation process a temperature of up to 245° C. The Trolox antioxidant has a higher boiling point than α-tocopherol; therefore, it is only necessary to add such antioxidant at the start of the synthesis in contrast to the situation with α-tocopherol.

TGA-analysis of PolyActive Granulate with Both Types of Antioxidants

Also, the Trolox antioxidant protects the PolyActive 70/30 material effectively. Thermogravimetric analysis (TGA) is an appropriate method for detecting weight losses of the material during exposure to thermal stress.

Figure 13A:
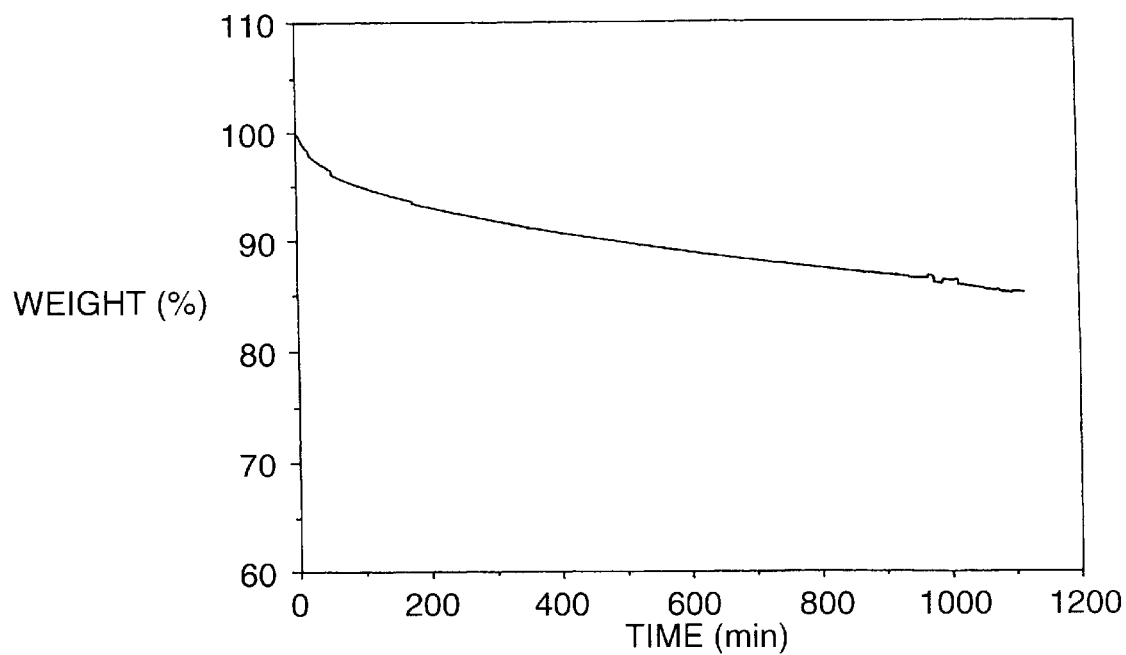
FIGS. 13A and 13B are graphs showing the degradation of PolyActive 70/30 treated with Trolox antioxidant or α-tocopherol.
Figure 13B:
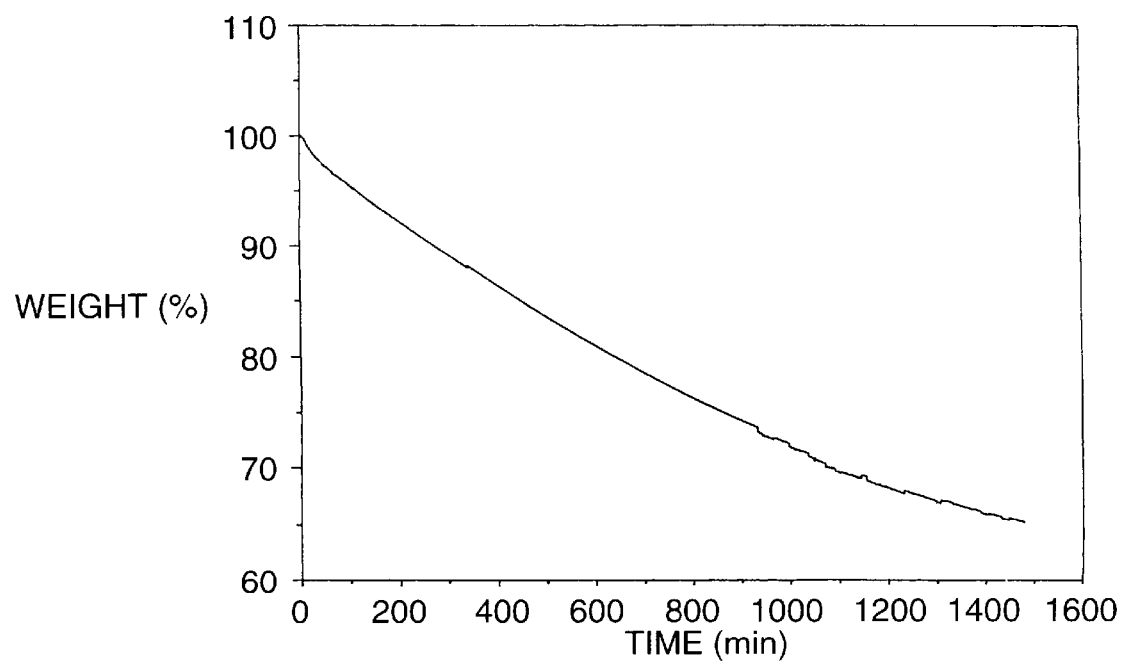

Weight loss could only be monitored for both formulations after a severe heat-pretreatment of the material for 17 days in a heat chamber at 100° C. The necessity of this pretreatment already indicates the stability and resistance to thermal influences of the new formulation. In FIGS. 13A and 13B it can be seen that after this pretreatment the formulation with the Trolox antioxidant degrades faster than the one with α-tocopherol under these conditions. The shown resistance of the new formulation however, to the applied thermal stress suggests a satisfactory shelf-life behavior under normal conditions.

In Vitro Degradation Results of 70/30 Rods Containing α-Tocopherol

Gamma-Radiated Rods

Figure 14A:
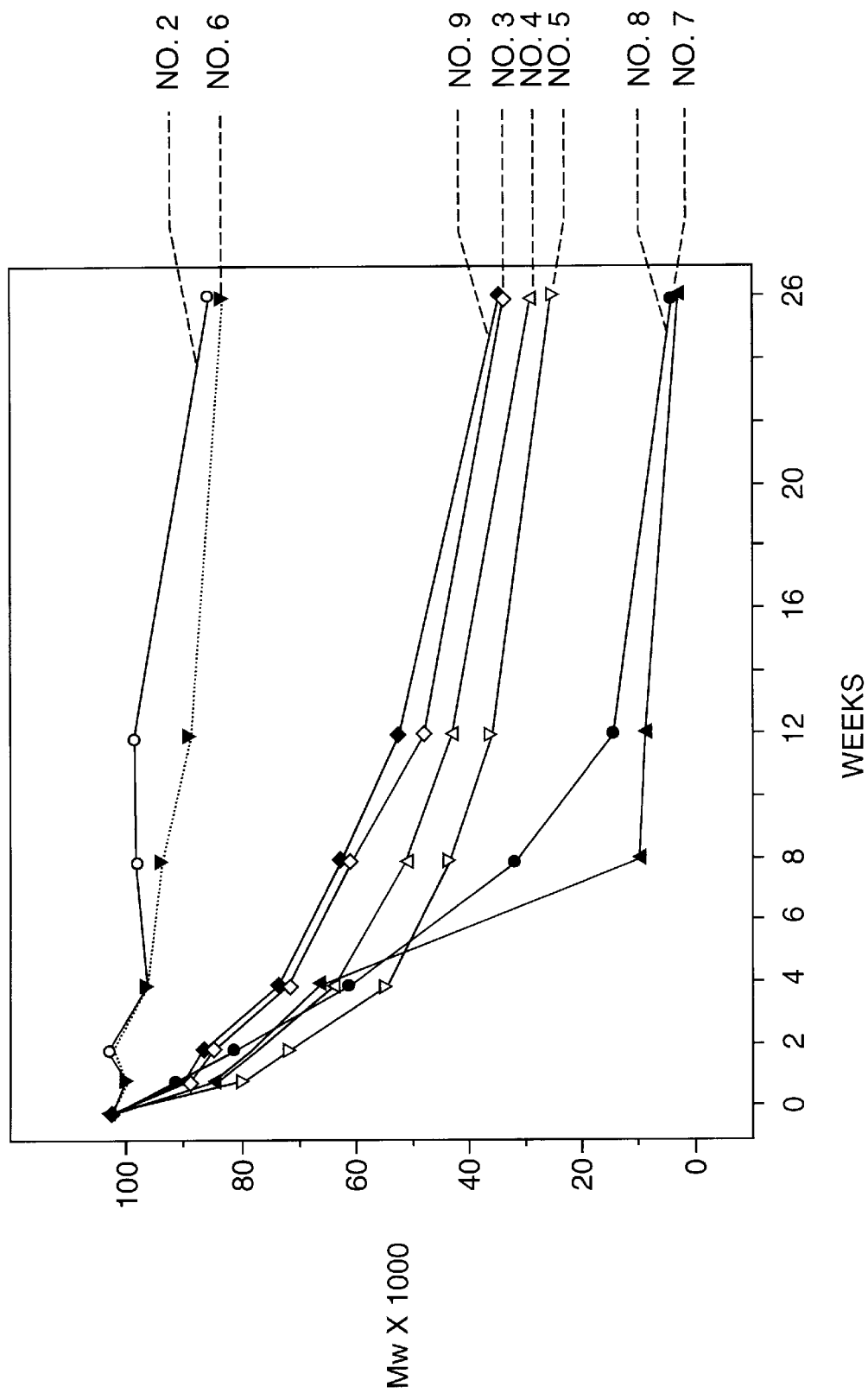
FIGS. 14A and 14B are graphs showing molecular weight profiles of 70/30 rods treated with gamma-radiation.
Figure 14B:
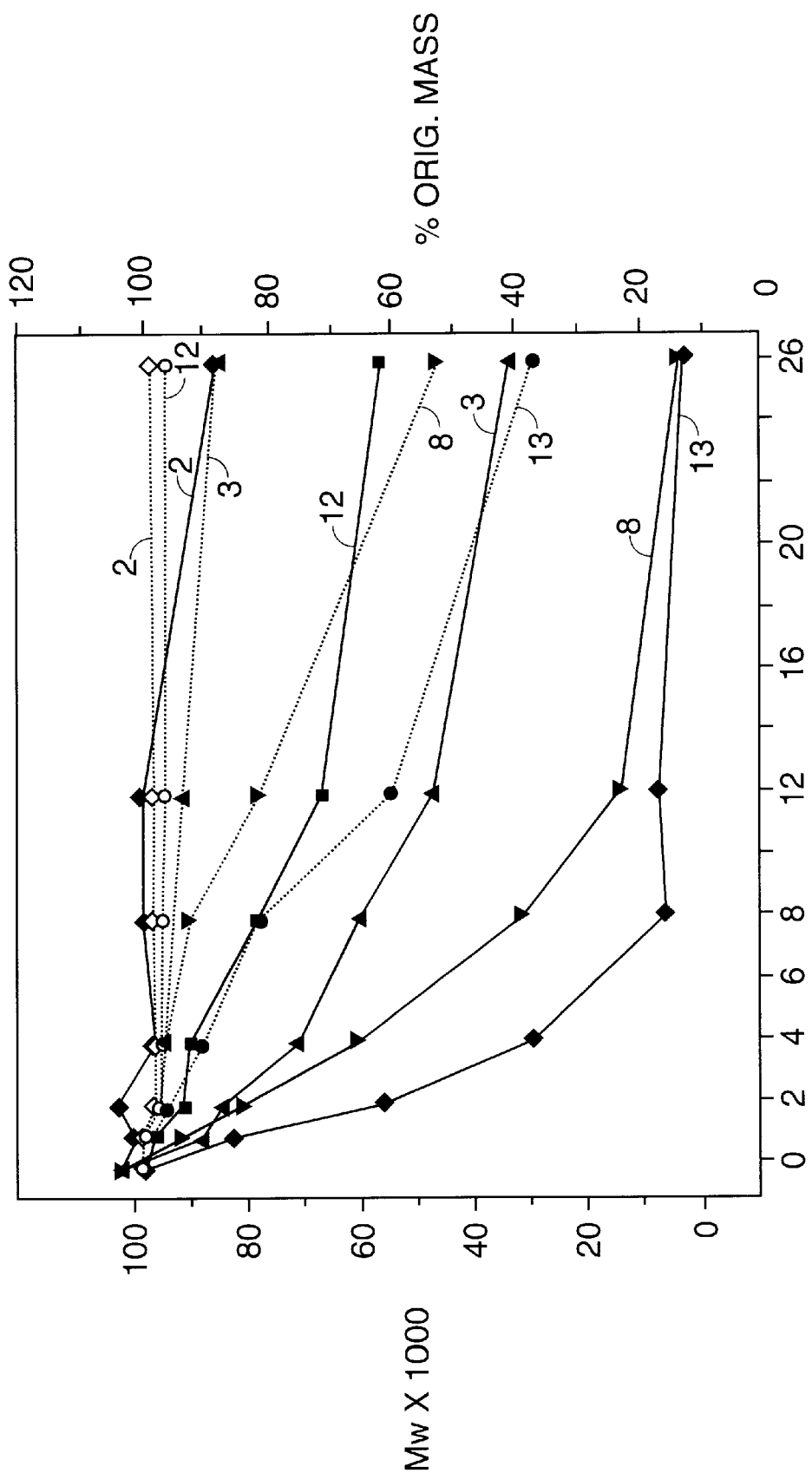

In FIGS. 14A and 14B molecular weight $M_w$-time profiles are depicted for the testing media numbers 2 through 9. (The profile for medium no. 1 is almost identical with that of medium no. 2 and for reasons of clarity is not depicted.)

It can be seen that there is almost no $M_w$-decrease in the water and 0.9% NaCl media. Up to 4 weeks $M_w$-decreasing rates in the phosphate buffered media and the $Fe/H_2O_2$ media are comparable. After 4 weeks the degrading influence of the $Fe/H_2O_2$ media on the 70/30 α-tocopherol rods is far more pronounced than that of the phosphate buffered media.

In the phosphate buffered media (nos. 3,4,5), after 8 weeks (including 7 medium changes), still more than half of the α-tocopherol quantity of timepoint zero is present in the device. In medium no. 5, half of the initial quantity is present after 26 weeks. In the oxidative $Fe/H_2O_2$ media (nos. 7,8) α-tocopherol has disappeared (i.e., reacted).

Thus, comparable $M_w$ decreases can be established with and without the consumption of α-tocopherol, for instance nos. 3,4,5,7,8,9 after 2 or 4 weeks.

Regarding the 3 phosphate buffers, it can be observed that the higher the phosphate concentration, the more α-tocopherol will remain; this suggests a specific "phosphate effect," such as iron-phosphate complexation or OH radical scavenging ability, rather than a non-specific pH-effect of the buffer on the $Fe/H_2O_2$ system.

The more pronounced influence of the $Fe/H_2O_2$ media after 4 weeks compared with the phosphate buffered media could be explained as follows. For oxidative chain-scission the concentration of available PEG remains relatively constant as is the case in media nos. 7 and 8. An almost linear $M_w$-decrease in the time can be observed. In contrast, the concentration available, hydrolysis-sensitive ester-bonds diminishes (nos. 3,4,5). All phosphate medium $M_w$-time curves level off.

The stabilizing influence of the phosphate buffers on the oxidative degradation of the PEGT/PBT material appears by comparison of the results from media nos. 3 and 9. The 20 mM phosphate buffer in medium no. 9 is able to prevent completely the extensive oxidative degradation ($M_w$-decrease) as occurred in medium no. 7. The profile of media nos. 3 and 9 are almost identical.

Non-Irradiated Rods

Figure 15:
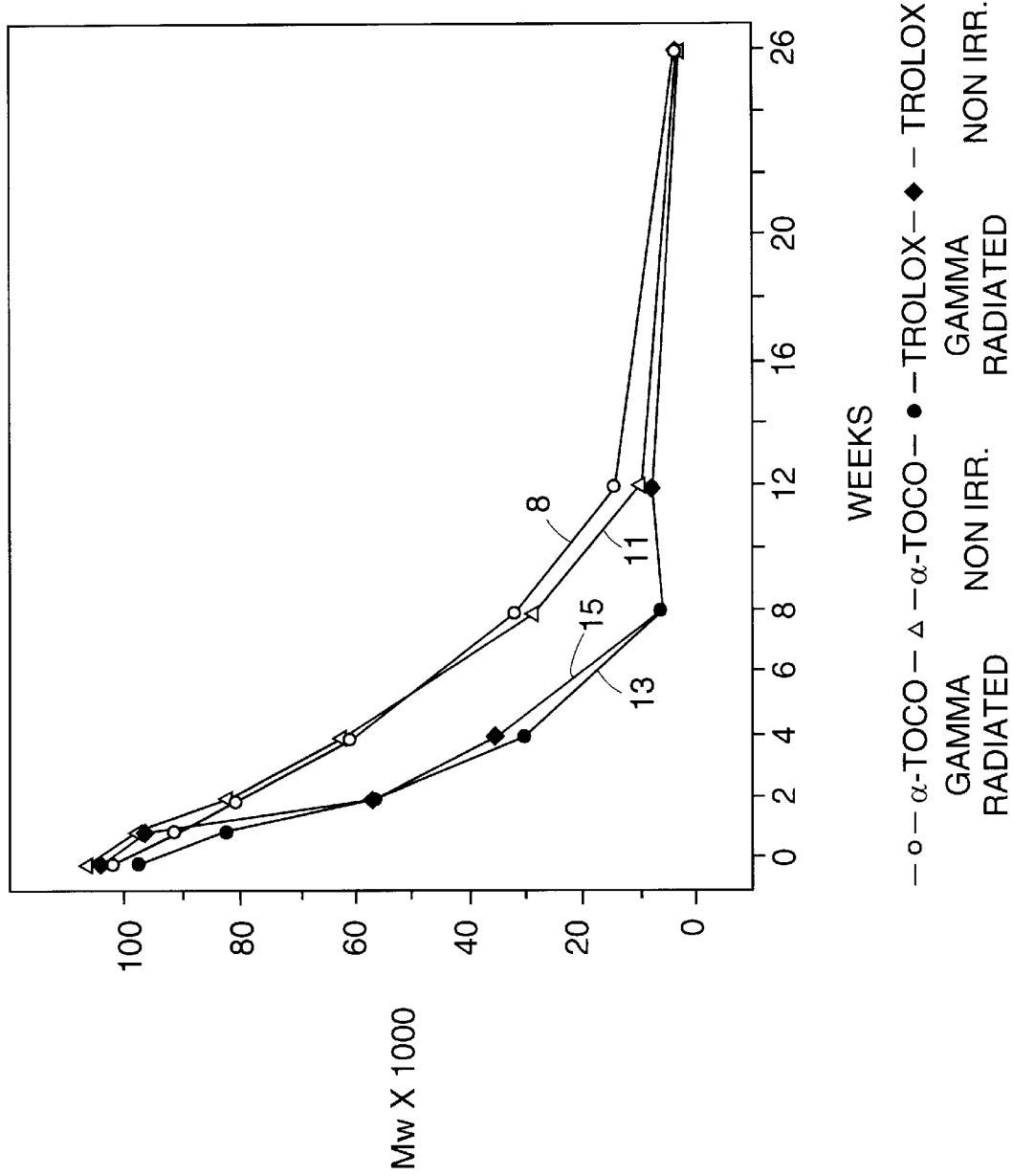
FIGS. 15 and 16 are graphs showing molecular weight profiles over time of gamma- radiated and non-irradiated PEGT/PBT rods treated with α-tocopherol.
Figure 16:
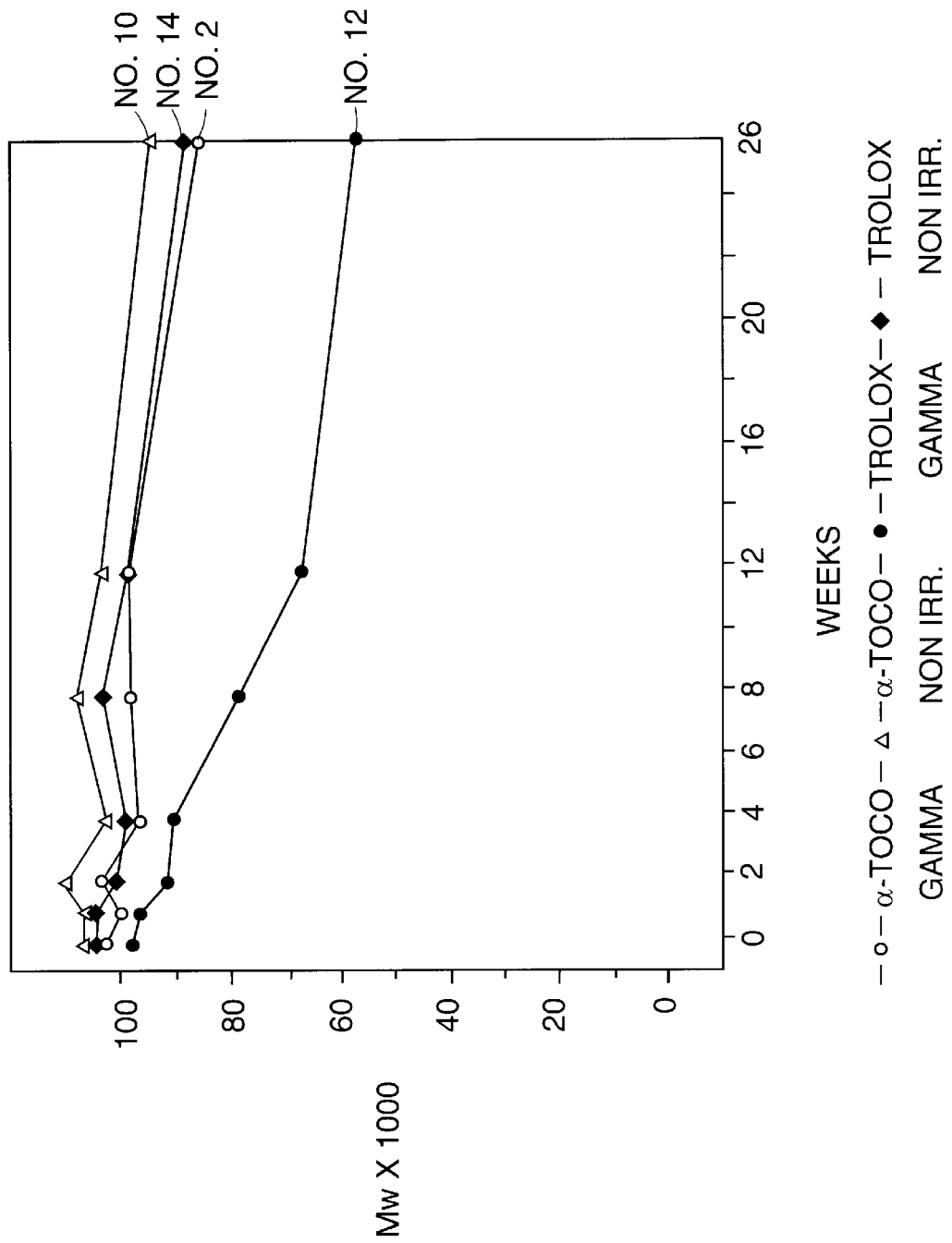

In FIGS. 15 and 16, the $M_w$-time profiles of gamma-irradiated and non-irradiated α-tocopherol containing rods are depicted, in the 0.9% $NaCl/Fe/H_2O_2$ medium and 0.9% NaCl medium, respectively.

Although gamma-radiation decreases the α-tocopherol content of 70/30 rods from 0.78% w/w to 0.51% w/w, the radiation does not influence the $M_w$ degradation behavior. $M_w$ decreasing profiles are almost identical.

In Vitro Degradation Results of 70/30 Rods Containing the Trolox-Derivative Antioxidant Gamma-Radiated Rods The degradation rate of the rods containing this type of antioxidant proceeds faster in the 0.9% $NaCl/Fe/H_2O_2$ medium than the rates of α-tocopherol rods (see FIG. 15).

In the 0.9% NaCl medium the gamma-irradiated rods with the hydrophilic antioxidant starts to degrade after 4 weeks, resulting in a 20% $M_w$-decrease after 8 weeks, 31% after 12 weeks, and 42% after 26 weeks.

Non-Irradiated Rods

In the 0.9% NaCl medium there is only slight degradation (no. 14)—a 16% $M_w$ decrease after 26 weeks.

The difference in $M_w$ degradation between both types of antioxidant formulations is extremely interesting for protein delivery applications. Larger proteins (e.g. vaccines) are restrained in the polymer matrix by their molecular size. Assuming that a release only starts at a (chain) degradation level corresponding with an $M_w$ of about 40,000, then it follows that in the 0.9% $NaCl/Fe/H_2O_2$ medium the "Trolox-derivative" matrix starts to release 4 weeks earlier than the "α-tocopherol" matrix. Considering the rigid oxidative stress of this medium, it is quite likely that the in vivo release starting times deviate more than 4 weeks. Another indication for a large difference in release times in vivo between the PEGT/PBT copolymers containing the different antioxidants is the large difference in $M_w$ loss between the two gamma-radiated matrices after 26 weeks. There was an 8% $M_w$ loss for the matrix containing α-tocopherol versus a 42% $M_w$ loss for the matrix including the Trolox derivative. Knowing these extremes, intermediate release starting times may be obtained by varying the ratio of the Trolox-derivative and α-tocopherol within the same matrix. By combining various matrices, for instance in the form of microspheres, with varying protein starting times, pulsatile release systems can be developed.

Mass Loss

In FIG. 14B both % original mass and $M_w$-time profiles are depicted for 5 selected media showing varying degradation rates.

The small percentage losses (ca. 0.5–1.5%) in the water and 0.9% NaCl media are caused by dissolution of the water-soluble PEG-butylene terephthalate (PEGT-BT) oligomers during the first week. Hereafter the weight remained fairly constant. Small variations are caused by deviations on the drying procedure or in humidity conditions.

This oligomer, with a chemical structure comprising $(BT)_x$ units, wherein x=1–20, with 1 or 2 pending PEG 1,000 chains, is the chemically non-incorporated oligomer from the copolymer-synthesis; through the hydrophilic PEG 1,000 and hydrophobic $(BT)_x$ moieties, it has the characteristics of a surfactant. Shaking of the solutions results in foaming.

In case of the Trolox-derivative rods mass losses in 0.9% NaCl are slightly larger than those of the α-tocopherol rods (nos. 12 and 14 versus nos. 2 and 10). This can be explained by loss of the water-soluble antioxidant itself (concentration approx. between 0.8 and 1.2% w/w)

Considering this, it is reasonable to assume that the percentages of remaining PEG-BT oligomer after synthesis using both types of antioxidant are comparable. This is confirmed by the observation of comparable peak surface areas of the PEG-BT oligomer resulting from HPLC terephthalate analysis.

It is expected that trends in mass loss are slower than those in $M_w$-decrease (FIG. 14B). Initially, only chain-scission occurs, at a later stage loss of degradation products proceeds. Some examples of varying $M_w$-decreases and mass losses can be found in the Table XII below.

It can be seen in this table and in FIG. 14B, that mass losses for the Trolox-derivative rods in the 0.9% NaCl/Fe/$H_2O_2$ medium are considerably larger than those of the α-tocopherol rods (nos. 8 and 11 versus nos. 13 and 15).

TABLE XII

| | | 8 weeks | | 12 weeks | | 26 weeks | |
|---|---|---|---|---|---|---|---|
| type of antioxidant | medium | % mass loss | % Mw loss | % mass loss | % Mw loss | % mass loss | % Mw loss |
| α-tocopherol | no. 3 | 4.8 | 40.5 | 6.5 | 46.6 | 11.6 | 40.5 |
| α-tocopherol | no. 7 | 9.4 | 90.4 | 27.7 | 88.1 | 58.1 | 96.1 |
| α-tocopherol | no. 8 | 7.5 | 68.8 | 18.7 | 85.8 | 47.7 | 95.8 |
| α-tocopherol | no. 11 | 7.9 | 72.5 | 18.6 | 89.8 | 50.7 | 96.1 |
| Trolox | no. 13 | 17.8 | 93.4 | 39.8 | 91.8 | 62.7 | 96.1 |
| Trolox | no. 15 | 17.4 | 94.4 | 35.4 | 92.7 | 60.1 | 96.2 |

$^1$H-NMR Measurements

By determining $^1$H-NMR changes with respect to the PEGT/PBT ratio, changes within the PEGT segment can be monitored. Only at the starting time point can the PEGT segment be calculated because it can be assumed at that time that the PEG chain has a molecular weight of 1000 Daltons. As soon as chain scission occurs such calculations are not possible due to varying PEG molecular weights. Instead of % PEGT calculations, characteristic signal ratios will be used which can show a decrease in the PEG-segment length: signal a=inner butylene protons

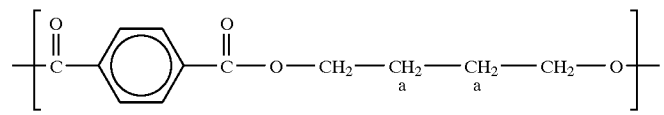

singal c=inner oxyethylene protons
c"=oxyethylene protons as indicated below
c'"=oxyethylene protons as indicated below

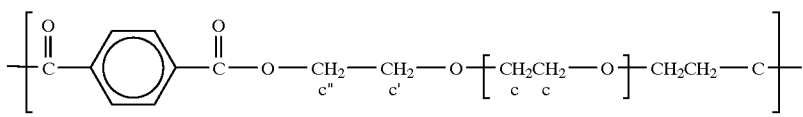

Ratio a/c reflects the ratio between the available quantity of the inner butylene protons and that of the inner oxethylene protons, and, therefore, is the measure for the ratio between the PEGT and PBT segment.

Using

70% PEGT, Mw PEGT 1130

30% PBT, Mw PBT 220 a/c is 0.1084

PEG: 1+20.3+1 oxyethylene units

Ratio (c'+c')/c reflects the ratio between the available quantity of the outer and inner oxyethylene units. In the case of progressing chain scission, this ratio will increase. Using (1+20.3+1) oxyethylene units for PEG, (c"+c')/c is 0.0985.

In Tables XIII and XIV below, these ratios are given after analysis of the device remnants for no. 4 (50 mM phosphate), no. 8 (NaCl/Fe/H$_2$O$_2$), and no. 13 (NaCl/Fe/H$_2$O$_2$ hydrophilic antioxidant) after 0, 4, 8, and 12 weeks.

It can be seen that the fast degrading device no. 13 shows the largest a/c ratios. The largest difference with no. 8 (α-tocopherol devices) is observed after 8 weeks; after 12 weeks the difference is smaller.

Regarding the (c"+c')/c ratio, no. 13 also reveals the largest values; however, there is a slight decrease after 8 weeks.

Possibly some measurement errors are made due to the fact that only dissolved copolymer remnant is measured by NMR; the higher the PBT content, the more difficult the dissolution behavior will be in the deuterated chloroform.

The general trend is clear, however, that the faster the degradation of a device is taking place is taking place (Mw, mass loss), the higher the resulting PBT-content present in the device remnant will be.

TABLE XIII

| a/c ratios of proton NMR signals | | | |
|---|---|---|---|
| | no. 4 | no. 8 | no. 13 |
| 0 weeks | 0.106 | 0.106 | 0.103 |
| | | | 0.103 |
| 4 weeks | 0.110 | 0.114 | 0.117 |
| | | | 0.124 |
| | | | 0.119 |
| 8 weeks | 0.114 | 0.113 | 0.162 |
| | 0.113 | 0.126 | 0.162 |
| | 0.113 | 0.125 | 0.167 |
| | | | 0.167 |
| 12 weeks | 0.117 | 0.161 | 0.179 |
| | 0.117 | 0.163 | 0.179 |

TABLE XIII

| (c" + c')/c ratios of proton NMR signals | | | |
|---|---|---|---|
| | no. 4 | no. 8 | no. 13 |
| 0 weeks | 0.098 | 0.098 | 0.095 |
| | | | 0.095 |
| 4 weeks | 0.097 | 0.105 | 0.104 |
| | | | 0.104 |
| | | | 0.102 |
| 8 weeks | 0.105 | 0.105 | 0.148 |
| | 0.099 | 0.097 | 0.149 |
| | 0.096 | 0.109 | 0.138 |
| | | | 0.135 |
| 12 weeks | 0.097 | 0.119 | 0.128 |
| | 0.94 | 0.110 | 0.127 |

Formation of Acid Degradation Products

In the weak-acid oxidative (NaCl)/Fe/H$_2$O$_2$ media, an additional acidificatino occurs. The start pH value of medium no. 7, 3.47, is within 5 weeks decreased to the fluctuating range of 2.77–3.13 (with one sample of medium no. 7 having a pH value of 3.35). The start pH value of medium no. 8, 3.65, is within 5 weeks decreased to 3.04–3.25, and for medium no. 13, about the same reduction is observed.

This acidification can only be explained by the formation of acids like formic acid and acetic acid (known oxidation products arising from PEG), rather than terephthalic acid, considering the fact that terephthalic acid (or a monofunctional derivative) is not able to establish pH values below 4 due to its high pK$_a$ value.

To confirm this, concentrations of formic acid and acetic acid in selected degradation solutions were measured by applying specific, enzymatic UV-tests commercially available for these carboxylic acids.

In Table XV below, concentrations of formic acid in μg/ml in selected solutions of media nos. 7, 8 and 11 are listed, as measured by a UV enzymatic test combination.

TABLE XV

| | medium no. 7 | medium no. 8 | medium no. 11 |
|---|---|---|---|
| week 2 | 37.51 | 9.29 | 10.40 |
| week 4 | 61.28 | 16.34 | 29.71 |
| week 6 | 78.37 | 30.08 | 34.17 |
| week 9 | 139.65 | 53.85 | 66.11 |
| week 12 | 137.05 | 81.71 | 97.31 |
| week 15 | 98.05 | 71.65 | 80.97 |

In Table XVI, these concentrations of formic acid are used to calculate the mole percent formation of formic acid from the available oxyethylene units, assuming 1 molecule of formic acid originates from 1 oxyethylene unit.

TABLE XVI

|         | medium no. 7 | medium no. 8 | medium no. 11 |
|---------|--------------|--------------|---------------|
| week 2  | 0.31         | 0.08         | 0.07          |
| week 4  | 0.50         | 0.13         | 0.23          |
| week 6  | 0.61         | 0.23         | 0.26          |
| week 9  | 1.08         | 0.43         | 0.46          |
| week 12 | 1.09         | 0.66         | 0.68          |
| week 15 | 0.73         | 0.53         | 0.60          |

In addition, cumulative percentages during the period of 15 weeks are given, as shown in Table XVII below.

For the most rapidly degrading medium, no. 7, this cumulative percentage, for 15 weeks, was about 11% (See Table XVII below). This predicts a long period during which this formic acid production will be continued. The resulting low pH value was measured up to 26 weeks.

TABLE XVII

Cumulative Molar Percentages of Formic Acid from Available Oxyethylene Units

|                    | no. 7 | no. 8 | no. 11 |
|--------------------|-------|-------|--------|
| cumul. % week 0–15 | 11.08 | 5.24  | 5.86   |

Figure 17:
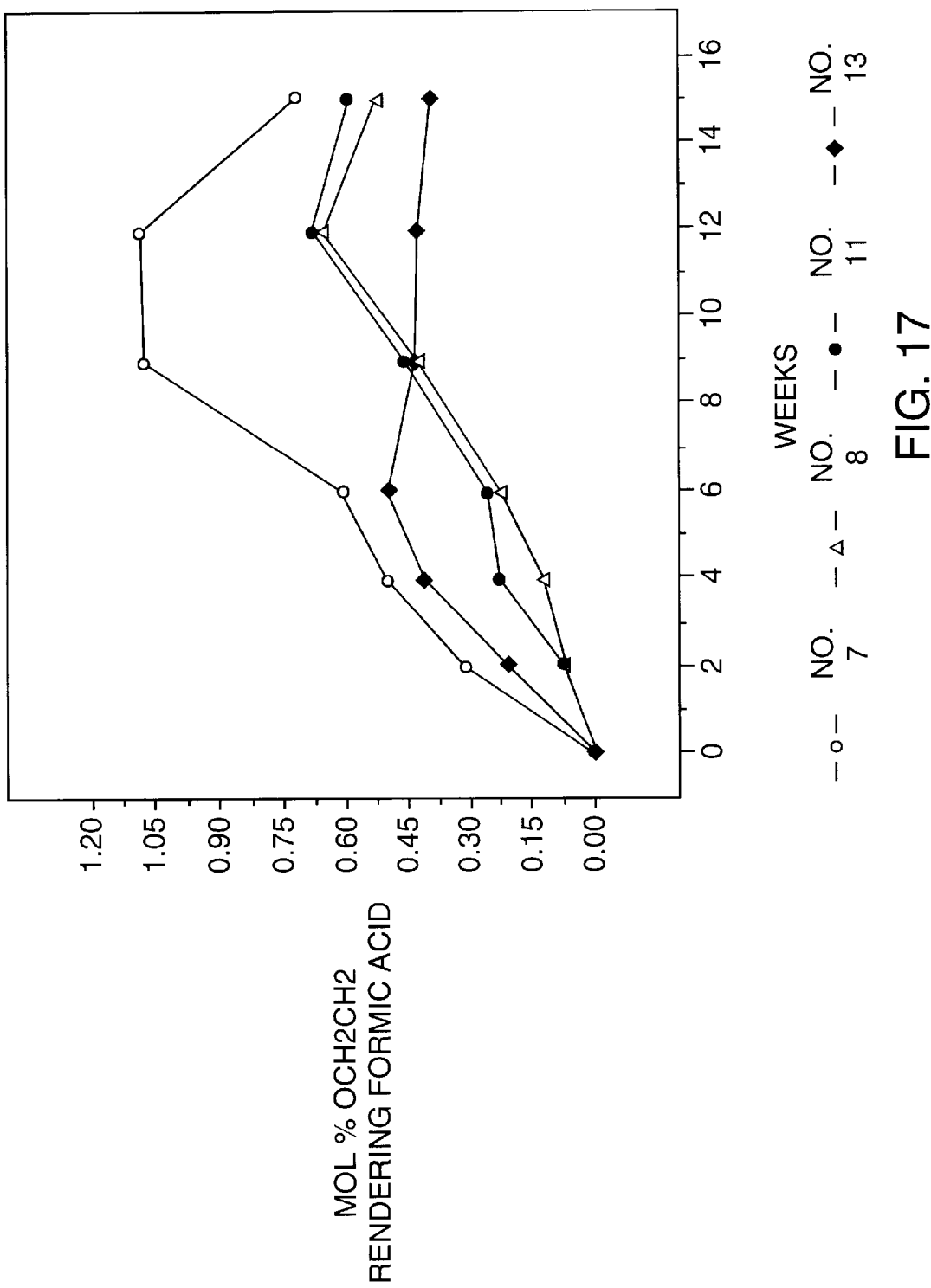
FIG. 17 is a graph showing formic acid formation over time from PEGT/PBT 70/30 rods.

In FIG. 17, the formic acid formation percentages for nos. 7, 8, 11 and 13 are depicted. It can be seen that in medium no. 7, $Fe/H_2O_2$ without NaCl, after 6 weeks, higher percentages of formic acid are built up in comparison with the other media. Again, there is no influence of gamma-irradiation (no. 8 versus no. 11).

During 0–6 weeks the formic acid concentrations produced in no. 13 (hydrophilic antioxidant) are somewhat higher than those in no. 8 ($\alpha$-tocopherol); however, the cumulative percentages after 15 weeks are comparable.

Apparently the faster degradation rate observed in no. 13, as reflected in $M_w$-decrease and mass loss, is not accompanied by a faster oxidative breakdown of PEG-units resulting in an increased acid production.

With the hydrophilic antioxidant, about the same pH values were found in the $NaCl/Fe/H_2O_2$ medium. After 26 weeks even slightly higher pH values were found, as shown in Table XVIII below.

TABLE XVIII

|                         | start pH | week 5 | week 10 | week 15 | week 20 | week 26 |
|-------------------------|----------|--------|---------|---------|---------|---------|
| α-toc. rods             |          |        |         |         |         |         |
| no. 8                   | 3.65     | 3.25   | 3.14    | 3.14    | 2.75    | 3.07    |
| no. 11                  | 3.65     | 3.26   | 3.15    | 3.13    | 3.03    | 3.08    |
| Trolox-derived rods     |          |        |         |         |         |         |
| no. 13                  | 3.47     | 3.09   | 3.13    | 3.19    | 3.05    | 3.15    |
| no. 15                  | 3.47     | 3.06   | 3.14    | 3.20    | 3.06    | 3.17    |

In Table XIX, concentrations of acetic acid ($\mu$g/ml) in selected solutions of media nos. 7, 8 and 11 are given.

On a molar basis the measured concentrations of acetic acid are 20–100× lower than the formic acid concentrations. The concentrations are measured by a UV enzymatic test combination.

TABLE XIX

|         | medium no. 7 | medium no. 8 | medium no. 11 |
|---------|--------------|--------------|---------------|
| week 2  | 0.30         | 0.72         | 0.09          |
| week 4  | 0.40         | 0.99         | 0.38          |
| week 6  | 0.72         | 0.75         | 0.50          |
| week 9  | 1.14         | 2.00         | 1.47          |
| week 12 | 1.01         | 1.80         | 1.88          |
| week 15 | 1.25         | 1.83         | 1.75          |
| week 20 | 1.25         | 1.29         | 1.80          |

Figure 18:
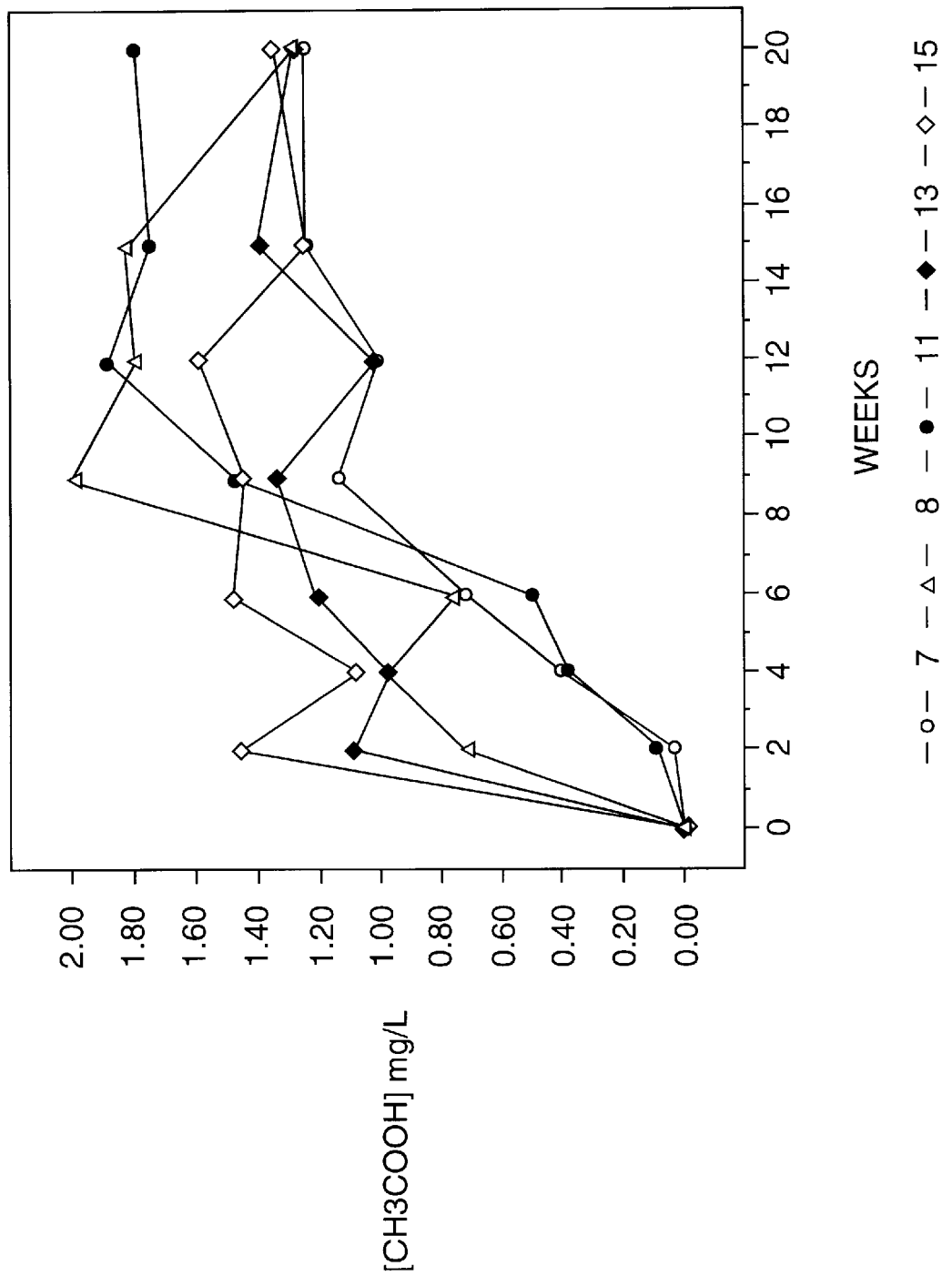
FIG. 18 is a graph showing acetic acid formation over time from PEGT/PBT 70/30 rods.

In FIG. 18, concentrations of acetic acid for media nos. 7, 8, 11, 13 and 15 are presented.

It can be concluded that the observed acidification in the strong oxidative media ($NaCl)/Fe/H_2O_2$ can be mainly ascribed to the formation of formic acid.

Acidification was only observed in the rigid oxidative ($NaCl)/Fe/H_2O_2$ environment. In all other media no acidification occurred (most likely) or was dominated by present buffer systems.

It should be stated, however, that this acidification is not to be expected in vivo. A "bulk-oxidation" as is the case in the rigid ($NaCl)/Fe/H_2O_2$ medium will not occur; in vivo the generation of reactive OH readicals takes only place in especially adapted structures within the cell of phagocytosing macrophages.

Therefore, fragmentation and particle size reduction of the copolymer material, and phagocytosis (a surface mediated process) are rate limiting steps in vivo. By this spreading in space and time of the degradation process the (reactive) aldehyde precursors of formic acid and acetic acid are effectively metabolized by enzyme systems from the cell. Most likely this will prevent any arising of free acids in the cytoplasm.

HPLC Terephthalate Analyses

70/30 Rods Containing α-Tocopherol (nos. 1–11)

In water and 0.9% NaCl (nos. 1, 2, 10) a characteristic pattern of peaks can be observed:

|                         | Retention time |
|-------------------------|----------------|
| terephthalic acid       | 2.3 min.       |
| "dimeric" terephthalate | 3 min.         |
| PEG-BT oligomer         | 4–8 min.       |
| unknown peak            | 12–14 min.     |

After one week all these compounds largely have been released. The chromatograms resulting from Week 2 solutions are almost empty.

The phosphate media (nos. 3, 4, 5, 9) and $(NaCl)/Fe/H_2O_2$ media (nos. 7, 8, 11) have other characteristic patterns. There are extra peaks and assemblies of peaks are present at the shorter retention times (immediately after terephthalic acid). The surface area of the PEGT-BT oligomer is usually smaller than that resulting from the water media, suggesting a partial degradation of the PEGT-BT oligomer into more hydrophilic (incorporation of oxygen) or into lower molecular weight products both resulting in shorter retention times.

Gamma-radiation does not influence any of the peak patterns. The chromatogram resulting from the water and 0.9% NaCl solutions remain almost empty during 2–12 weeks; no degradation is taking place.

The peak assembly areas in the chromatogram resulting from the phosphate- and oxidative media diminish in size during 2 and 4 weeks. However, from Week 6 the surface area of the "oxidative" peak pattern increases again.

70/30 Rods Containing the Trolox-Derivative Antioxidant

After Week 1, the peak patterns in the chromatogram from the Trolox-derivative rods in the 0.9% NaCl media (nos. 12, 14) are almost identical with those from the α-tocopherol rods (nos. 2, 10).

Again, no influence of gamma-radiation could be observed.

The chromatograms showed that in synthesis using both α-tocopherol as well as the Trolox-derivative, the portion of the non-incorporated PEG-BT oligomer is formed in the same degree. This indicated that the type of antioxidant does not influence the polymerization process.

Also, the peak patterns resulting from the phosphate and (NaCl)/Fe/$H_2O_2$ media are almost identical after Week 1.

From Week 2 the surface area of the "oxidative" peak patterns increases. From Week 4 the enlarged surface area of the peak assembly remains constant regarding shape and magnitude. The surface area of the "oxidative" peak pattern of the Trolox-derivative rods (nos. 13, 15) are always considerably larger than those of the corresponding α-tocopherol rods (nos. 8, 11).

Comparing the terephthalate chromatograms in time resulting from the α-tocopherol and the Trolox-derivative rods, i.e., nos. 8 versus nos. 13 and nos. 11 versus nos. 15, it was found that only quantitative differences exist. The released terephthalates should explain at least part, and possibly the largest part, of the difference in mass loss between both types of antioxidant formulations.

Considering the almost identical pH values, it may be concluded that the more extensive degradation with the hydrophilic antioxidant is caused predominantly by more extensive PEG-chain scissions, resulting in higher concentrations of terephthalate derivatives, lower $M_w$ values and larger mass losses. These increased PEG-chain scissions, however, are not accompanied by increased oxidative consumption of oxyethylene units leading to acid products.

It is to be understood, however, that the scope of the present invention is not to be limited to the specific embodiments described above. The invention may be practiced other than as particularly described and still be within the scope of the accompanying claims.

What is claimed is:

1. A composition for delivering a biologically active agent to a host comprising a biologically active agent encapsulated in a microsphere comprising a polyetherester copolymer comprised of the following recurring units:

—OLO—CO—R—CO—, wherein L is a divalent radical remaining after removal of terminal hydroxy groups from a poly(oxyalkylene)glycol, and

—ORE—CO—R—CO—, wherein E is an organic radical selected from the group consisting of a substituted or unsubstituted alkylene radical having from 2 to 8 carbon atoms, and R is a divalent radical remaining after removal of carboxyl groups from a dicarboxylic acid.

2. A composition for delivering a biologically active agent to a host comprising a biologically active agent encapsulated in a microsphere comprising a polyetherester copolymer comprising a plurality of recurring units of a first component and of a second component, wherein said first component comprises form about 30 wt. % to about 99 wt. %, based on the weight of said copolymer, of units of the formula:

—OLO—CO—R—CO—, wherein L is a divalent radical remaining after removal of terminal hydroxyl groups from a poly(oxyalkylene)glycol, and said second component comprises from about 1 wt. % to about 70 wt. %, based upon the weight of said copolymer, of units having the formula:

—OEO—CO—R—CO—, wherein E is an organic radical selected from the group consisting of a substituted or unsubstituted alkylene radical having form 2 to 8 carbon atoms, and R is a divalent radical remaining after removal of carboxyl groups from a dicarboxylic acid.

3. The composition of claim 1 wherein said polyalkylene glycol is selected from the group consisting of polyethylene glycol, polypropylene glycol and polybutylene glycol.

4. The composition of claim 3 wherein said polyalkylene glycol is polyethylene glycol.

5. The composition of claim 1 wherein said polyester is selected from the group consisting of polyethylene terephthalate, polypropylene terephthalate, and polybutylene terephthalate.

6. The composition of claim 5 wherein said polyester is polybutylene terephthalate.

7. The composition of claim 1 wherein said copolymer is a polyethylene glycol/polybutylene terephthalate copolymer.

8. The composition of claim 1 wherein said polyester is comprised of units having the following structural formula:

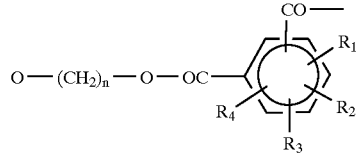

wherein n is from 2 to 8, and each of $R_1$, $R_2$, $R_3$, and $R_4$ is hydrogen, chlorine, nitro-, or alkoxy, and each of $R_1$, $R_2$, $R_3$, and $R_4$ is the same or different.

9. The composition of claim 2 wherein L is a poly (oxyalkylene)glycol selected from the group consisting of poly(oxyethylene)glycol, poly(oxypropylene)glycol, and poly(oxybutylene)glycol.

10. The composition of claim 9 wherein said poly (oxyalkylene)glycol is poly(oxyethylene)glycol.

11. The composition of claim 2 wherein E is an alkylene radical having from 2 to 4 carbon atoms.

12. The composition of claim 11 wherein said second component is selected from the group consisting of polyethylene terephthalate, polypropylene terephthalate, and polybutylene terephthalate.

13. The composition of claim 12 wherein said second component is polybutylene terephthalate.

14. The composition of claim 2 wherein L is a poly (oxyethylene)glycol, said second component is polybutylene terephthalate, and said copolymer is a polyethylene glycol terephthalate/polybutylene terephthalate copolymer.

15. The composition of claim 14 wherein said biologically active agent is a non-peptide, non-protein drug having a molecular weight which is less than 500.

16. The composition of claim 15 wherein the polyethylene glycol component of said copolymer has a molecular weight of from about 200 to about 400.

17. The composition of claim 15 wherein said polyethylene glycol terephthalate is present in an amount of from about 30 wt. % to about 80 wt. % of the weight of the copolymer, and said polybutylene terephthalate is present in the copolymer in an amount of from about 20 wt. % to about 70 wt. % of the weight of the copolymer.

18. The composition of claim 17 wherein said polyethylene glycol terephthalate is present in an amount of from about 50 wt. % to about 60 wt. % of the weight of the copolymer, and said polybutylene terephthalate is present in an amount of from about 40 wt. % to about 50 wt. % of the weight of the copolymer.

19. The composition of claim 15 wherein said matrix further includes at least one hydrophobic antioxidant.

20. The composition of claim 19 wherein said at least one hydrophobic antioxidant is present in an amount of from about 0.5 wt. % to about 2 wt. % of the total weight of the matrix.

21. The composition of claim 19 wherein said at least one hydrophobic antioxidant is α-tocopherol.

22. The composition of claim 15 wherein terephthalate of said copolymer is replaced with succinate in an amount of from about 0.1 mole % to about 20 mole %.

23. The composition of claim 22 wherein said terephthalate is replaced with succinate in an amount of from about 0.1 mole % to about 5 mole %.

24. The composition of claim 15 wherein butylene of said copolymer is replaced with diethyleneglycol in an amount of from about 0.1 mole % to about 22 mole %.

25. The composition of claim 24 wherein said butylene is replaced with diethyleneglycol in an amount of from about 0.5 mole % to about 2 mole %.

26. The composition of claim 14 wherein said agent is selected from the group consisting of biologically active peptides and biologically active proteins.

27. The composition of claim 26 wherein said biologically active agent is a protein having a molecular weight of greater than 10,000.

28. The composition of claim 27 wherein said polyethylene glycol component of said copolymer has a molecular weight of from about 1,000 to about 20,000.

29. The composition of claim 27 wherein said polyethylene glycol terephthalate is present in said copolymer in an amount of from about 30 wt. % to about 90 wt. % of the weight of the copolymer, and said polybutylene terephthalate is present in said copolymer in an amount of from about 10 wt. % to about 70 wt. % of the weight of said copolymer.

30. The composition of claim 29 wherein said polyethylene glycol terephthalate is present in an amount of from about 60 wt. % to about 70 wt. % of the weight of said copolymer, and said polybutylene terephthalate is present in an amount of from about 30 wt. % to about 40 wt. % of the weight of said copolymer.

31. The composition of claim 27 wherein said matrix further comprises a hydrophilic antioxidant.

32. The composition of claim 31 wherein said hydrophilic antioxidant has the following structural formula:

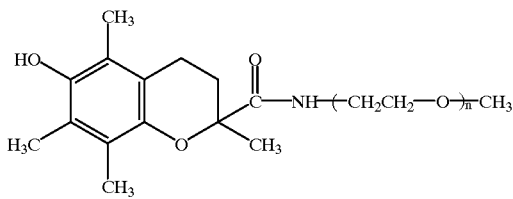

wherein n is 21 or 22.

33. The composition of claim 31 wherein said hydrophilic antioxidant is present in said matrix in an amount of from about 1.0 wt. % to about 5.0 wt. % of the total weight of the matrix.

34. The composition of claim 27 wherein said matrix further includes up to about 10 wt. %, based on the weight of said copolymer, of polyethylene glycol having a molecular weight of from about 4,000 to about 10,000.

35. The composition of claim 26 wherein said agent is a biologically active peptide or a biologically active protein having a molecular weight less than 10,000.

36. The composition of claim 35 wherein said polyethylene glycol has a molecular weight of from about 200 to about 6,000.

37. The composition of claim 35 wherein first component is present in said copolymer in an amount of from about 30 wt. % to about 80 wt. % based on the weight of said copolymer, and said polybutylene terephthalate is present in an amount of from about 20 wt. % to about 70 wt. % based on the weight of said copolymer.

38. The composition of claim 35 wherein said matrix further comprises at least one hydrophilic antioxidant.

39. The composition of claim 38 wherein said matrix further includes from about 1 wt. % to about 10 wt. %, based on the weight of said copolymer, of polyethylene glycol having a molecular weight of from about 1,000 to about 4,000.

40. A process for delivering a biologically active agent to a host in need thereof comprising:
    administering to said host a composition comprising a biologically active agent encapsulated in a microsphere comprising a polyetherester copolymer comprising a first component including units having the formula:

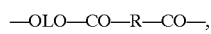

wherein L is a divalent radical remaining after removal of terminal hydroxy groups from a poly(oxyalkylene)glycol, and
    a second component including units having the formula:

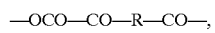

wherein E is an organic radical selected from the group consisting of a substituted or unsubstituted alkylene radical having from 2 to 8 carbon atoms, and R is a divalent radical remaining after removal of carboxyl groups from a dicarboxylic acid, said composition being administered in an amount effective to provide a therapeutic or prophylactic effect in said host.

41. A process for delivering a biologically active agent to a host in need thereof, comprising:
    administering to said host a composition comprising a biologically active agent encapsulated in a microsphere comprising a polyetherester copolymer comprising a plurality of recurring units of a first component and of a second component, wherein said first component comprises from about 30 wt. % to about 99 wt. %, based on the weight of said copolymer, of units of the formula:

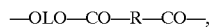

wherein L is a
    divalent radical remaining after removal of terminal hydroxyl groups from a poly(oxyalkylene)glycol, and said second component comprises from about 1 wt. % to about 70 wt. % based upon the weight of the copolymer, of units having the formula:

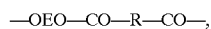

wherein E is an organic radical selected from the group consisting of a substituted or unsubstituted alkylene radical having from 2 to 8 carbon atoms, and R is a divalent radical remaining after removal of carboxyl groups from a dicarboxylic acid, said composition being administered in an amount effective to provide a therapeutic or prophylactic effect in said host.

42. The composition of claim 2 wherein said microsphere has a diameter of up to 1,000 microns.

43. The method of claim 41 wherein said microsphere is delivered orally.

44. The method of claim 42 wherein said microsphere has a diameter of from about 0.1 micron to about 1,000 microns.

45. The method of claim 44 wherein said microsphere has a diameter of from about 1 micron to about 10 microns.

46. The method of claim 45 wherein said microsphere has a diameter of from about 1 micron to about 5 microns.

47. The method of claim 46 wherein said microsphere has a diameter of from about 1 micron to about 30 microns.

48. The method of claim 47 wherein said microsphere has a diameter of from about 10 microns to about 20 microns.

* * * * *

UNITED STATES PATENT AND TRADEMARK OFFICE
CERTIFICATE OF CORRECTION

| | | |
|---|---|---|
| PATENT NO. | : 5,980,948 | |
| APPLICATION NO. | : 08/699896 | |
| DATED | : November 9, 1999 | |
| INVENTOR(S) | : Jaap H. Goedemoed et al. | |

It is certified that error appears in the above-identified patent and that said Letters Patent is hereby corrected as shown below:

Column 39, line 51, please delete "-ORE-CO-R-CO-," and replace with -- -OEO-CO-R-CO-, --
Column 39, line 62, please delete "form" and replace with -- from --
Column 40, line 7, please delete "form" and replace with -- from --
Column 40, line 30, please delete the second occurrence of "O-" in the structural formula
Column 41, line 22, please delete "22" and replace with -- 20 --
Column 42, line 36, please delete "-OCO-CO-R-CO-," and replace with -- -OEO-CO-R-CO-, --

Signed and Sealed this
Twenty-seventh Day of September, 2011

David J. Kappos
*Director of the United States Patent and Trademark Office*